(12) United States Patent
Sharma et al.

(10) Patent No.: US 11,642,018 B1
(45) Date of Patent: May 9, 2023

(54) VOLUMETRIC DEPTH IMAGING FOR LENS FIT

(71) Applicant: Meta Platforms Technologies, LLC, Menlo Park, CA (US)

(72) Inventors: Robin Sharma, Redmond, WA (US); Mohamed Tarek El-Haddad, Redmond, WA (US); Ruobing Qian, Durham, NC (US); Byron Taylor, Sammamish, WA (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 117 days.

(21) Appl. No.: 16/743,985

(22) Filed: Jan. 15, 2020

(51) Int. Cl.
  *A61B 3/10* (2006.01)
  *G02B 27/01* (2006.01)
  *A61B 5/00* (2006.01)
  *G02C 7/02* (2006.01)

(52) U.S. Cl.
  CPC ........... *A61B 3/102* (2013.01); *A61B 5/0066* (2013.01); *G02B 27/0172* (2013.01); *G02B 2027/0178* (2013.01); *G02C 7/027* (2013.01)

(58) Field of Classification Search
  CPC .. A61B 3/102; A61B 5/0066; G02B 27/0172; G02B 27/0178; G02B 2027/0178; G02C 7/027
  USPC ........................................................ 351/205
  See application file for complete search history.

(56) References Cited

U.S. PATENT DOCUMENTS

| 10,664,953 | B1 * | 5/2020 | Lanman | ................. | G06T 5/002 |
|---|---|---|---|---|---|
| 2002/0176052 | A1 | 11/2002 | Ueno | | |
| 2006/0098293 | A1 * | 5/2006 | Garoutte | ............ | G02B 27/0172 |
| | | | | | 359/630 |
| 2008/0052194 | A1 | 2/2008 | Shinohara et al. | | |
| 2010/0149492 | A1 | 6/2010 | Allione et al. | | |
| 2011/0051079 | A1 | 3/2011 | Martinez et al. | | |
| 2011/0299034 | A1 * | 12/2011 | Walsh | ................. | A61B 5/0073 |
| | | | | | 351/206 |
| 2015/0055086 | A1 | 2/2015 | Fonte et al. | | |
| 2016/0103335 | A1 * | 4/2016 | Ben-Shahar | ............. | G02C 1/00 |
| | | | | | 351/158 |
| 2016/0299360 | A1 * | 10/2016 | Fonte | ..................... | G06T 19/20 |
| 2018/0017815 | A1 | 1/2018 | Chumbley et al. | | |
| 2018/0136486 | A1 * | 5/2018 | Macnamara | ......... | A61B 3/0025 |

(Continued)

FOREIGN PATENT DOCUMENTS

JP      2018201858 A   * 12/2018

OTHER PUBLICATIONS

Song, Shaozhen, et al., Long-range and wide field of view optical coherence tomography . . . , Biomedical Optics Express 4734, Nov. 1, 2016, 15, vol. 7.

(Continued)

*Primary Examiner* — Collin X Beatty
(74) *Attorney, Agent, or Firm* — Freestone Intellectual Property Law PLLC; Aaron J. Visbeek

(57) ABSTRACT

A volumetric depth image is captured. The volumetric depth image includes a front surface of a prescription lens, a back surface of the prescription lens, and a cornea of an eye of a wearer of the prescription lens. Lens-to-eye data is determined from the volumetric depth image. The lens-to-eye data includes measurements of the prescription lens with respect to the eye. A three-dimensional (3D) optical-mechanical fit profile is generated or the wearer based on the lens-to-eye data.

20 Claims, 18 Drawing Sheets

(56) References Cited

U.S. PATENT DOCUMENTS

| | | |
|---|---|---|
| 2018/0356639 A1 | 12/2018 | Schaefer et al. |
| 2021/0088327 A1* | 3/2021 | Tao .................... G01L 1/183 |
| 2021/0125314 A1* | 4/2021 | Jones .................... G06T 15/04 |
| 2021/0271117 A1 | 9/2021 | Le Cain et al. |

OTHER PUBLICATIONS

Fechtig, Daniel J., et al., Line-field parallel sweptsource MHz OCT for structural and functional retinal imaging, Biomedical Optics Express 735, Mar. 1, 2015, 20, vol. 6. No. 3.

Thouvenin, Olivier, et al., En face coherence microscopy [Invited], Biomedical Optics Express 622, Feb. 1, 2017, 18, vol. 8 No. 2.

Graj Ciar, Branislav, et al., Parallel Fourier domain optical coherence tomography for in vivo measurement of the human eye, Optics Express 1137, Feb. 21, 2005, 18, vol. 13, No. 4.

Grieve, Kate, In vivo anterior segment imaging in the rat eye with high speed white light full-field optical coherence tomography, Optics Express 6295, Aug. 8, 2005, 10, vol. 13.

Non-Final Office Action dated Mar. 4, 2022 for U.S. Appl. No. 16/743,689, filed Jan. 15, 2020, 15 pages.

Non-Final Office Action dated Apr. 18, 2022 for U.S. Appl. No. 16/743,689, filed Jan. 15, 2020, 7 pages.

Non-Final Office Action dated Apr. 18, 2022 for U.S. Appl. No. 16/743,950, filed Jan. 15, 2020, 9 pages.

\* cited by examiner

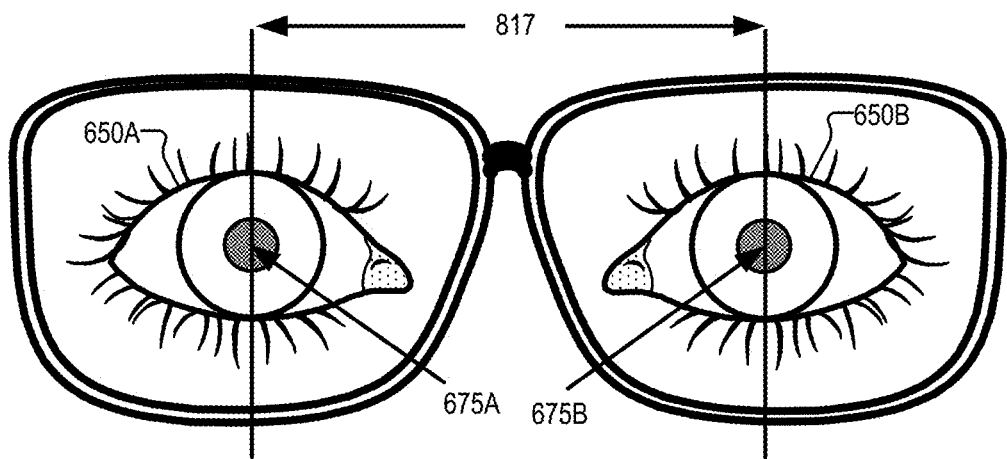
FIG. 8A
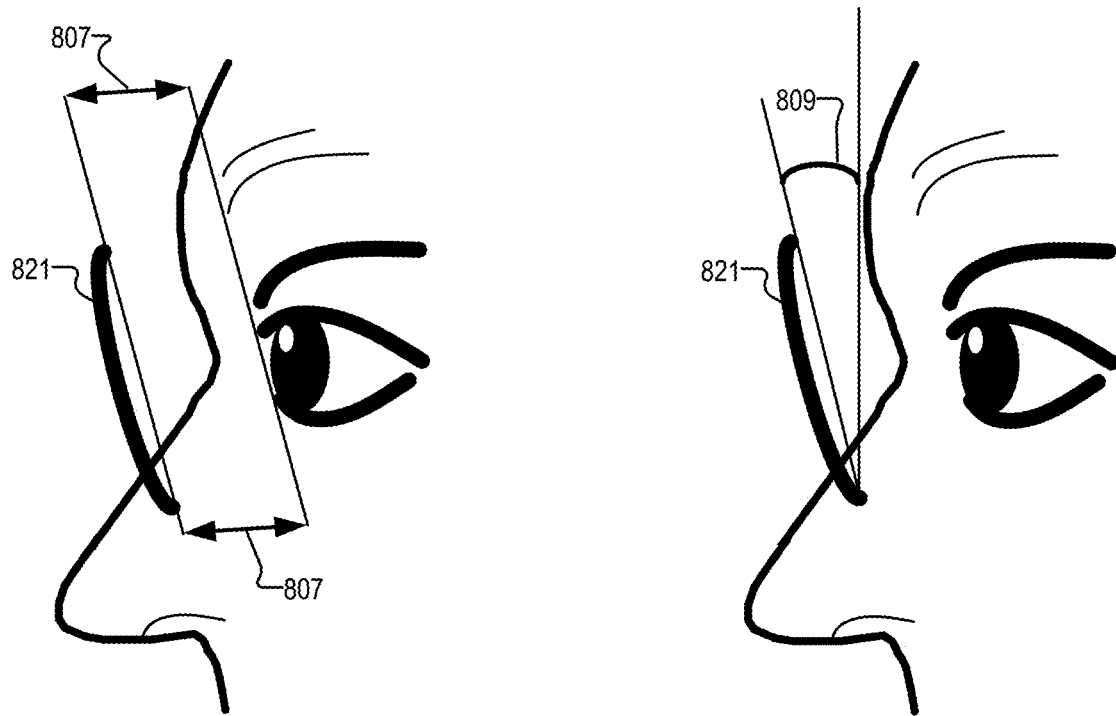
FIG. 8B  FIG. 8C

VOLUMETRIC DEPTH IMAGING FOR LENS FIT

CROSS-REFERENCE TO RELATED APPLICATIONS

This application is related to U.S. non-provisional patent applications entitled, "Prescription Optical Element for Selected Head Mounted Device" and "Prescription Optical Element Based on Optical-Mechanical Profile," filed the same day.

BACKGROUND INFORMATION

Obtaining prescription eyeglasses typically includes taking an eyeglass prescription to an optician or other optical professional and selecting eye-glass frames to hold the corrective lenses. Some consumers who are switching from one pair of eyeglasses to a new pair of eyeglasses report a transition period (measured in minutes, days, or even weeks) to get used to the new eyeglasses. Some consumers also notice a transition period when switching between two different eyeglasses that the consumer already owns, even when the optical power of the two different eyeglasses are the same.

BRIEF DESCRIPTION OF THE DRAWINGS

Non-limiting and non-exhaustive embodiments of the invention are described with reference to the following figures, wherein like reference numerals refer to like parts throughout the various views unless otherwise specified.

FIGS. 8A-8C illustrate various measurements from a volumetric depth image, in accordance with aspects of the disclosure.

DETAILED DESCRIPTION

In the following description, numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Embodiments of this disclosure include capturing a volumetric depth image that includes one or two prescription lenses with respect to the eye and/or face of a wearer of the prescription lenses. The volumetric depth image may be captured by optical coherence tomography (OCT) techniques, in some embodiments. From the volumetric depth image a three-dimensional (3D) optical-mechanical fit profile can be generated that is specific to a wearer of the prescription lenses. The 3D optical-mechanical fit profile can then be utilized to decrease the discomfort that the user experiences during the transition period for a wearer to get used to switching between different prescription lenses. In one particular context, the 3D optical-mechanical fit profile can be utilized to reduce the transition period between a person switching from prescription eyeglasses and augmented reality (AR) glasses that include lenses with optical power.

Literature associated with the field of optometry suggests that differences in lenses and frames may account for a transition period when a person switches between corrective lenses. For example, differences in eye-relief, interpupillary distance (IPD), frame tilt angle, refractive material of lenses, residual aberrations, size of lenses, and/or base curve may contribute to a transition period where a person gets used to new corrective lenses. Measuring and/or correcting for at least some of these factors may allow for designing and fabricating corrective lenses for head mounted devices such as AR glasses that reduce or eliminate a transition period for a user. These and other embodiments are described in more detail in connections with FIGS. 1-14.

Figure 1:
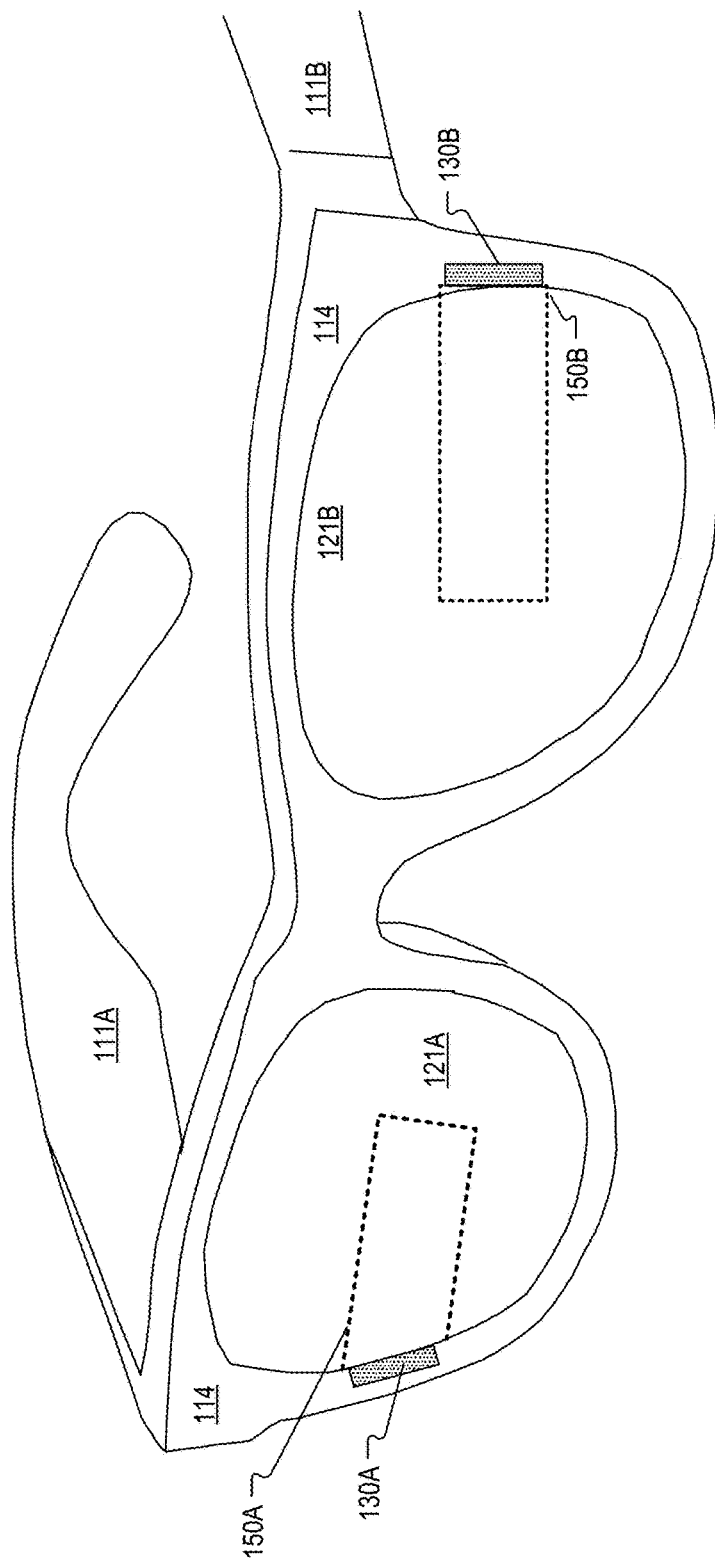
FIG. 1 illustrates an example head mounted device that may include corrective lenses that are fabricated based on a three-dimensional (3D) optical-mechanical fit profile of a user generated by a volumetric depth image of the user wearing eyeglasses with corrective lenses, in accordance with aspects of the disclosure.

FIG. 1 illustrates an example head mounted device 100 that may include corrective lenses 121 that are fabricated based on a 3D optical-mechanical fit profile of a user generated by a volumetric depth image of the user wearing eyeglasses with corrective lenses, in accordance with aspects of the disclosure. Head mounted device 100 may be considered an AR or mixed reality (MR) head mounted display, in some aspects of the disclosure. In some aspects, head mounted device 100 does not necessarily include a display but does include electronics of some kind such as one or more cameras, speakers, eye-tracking sensor modules, other sensors, processors, and/or memory.

In FIG. 1, example head mounted device 100 includes frame 114 coupled to arms 111A and 111B. Lenses 121A and 121B are mounted to frame 114. Lenses 121 may include optical power matched to a particular wearer of head mounted device 100. The illustrated head mounted device 100 is configured to be worn on or about a head of a user.

Each lens 121 may optionally include a waveguide 150 to direct image light generated by a display 130 to an eyebox area for viewing by a wearer of head mounted device 100. Display 130 may include an LCD, an organic light emitting diode (OLED) display, micro-LED display, quantum dot display, pico-projector, or liquid crystal on silicon (LCOS) display for directing image light to a wearer of head mounted device 100.

The frame 114 and arms 111 of the head mounted device 100 may include supporting hardware of head mounted device 100. Head mounted device 100 may include any of processing logic, wired and/or wireless data interface for sending and receiving data, graphic processors, and one or more memories for storing data and computer-executable instructions. In one embodiment, head mounted device 100 may be configured to receive wired power. In one embodiment, head mounted device 100 is configured to be powered by one or more batteries. In one embodiment, head mounted device 100 may be configured to receive wired data including video data via a wired communication channel. In one embodiment, head mounted device 100 is configured to receive wireless data including video data via a wireless communication channel.

Lenses 121 may appear transparent to a user to facilitate augmented reality or mixed reality where a user can view scene light from the environment around her while also receiving image light directed to her eye(s) by waveguide(s) 150. Consequently, lenses 121 may be considered (or include) an optical combiner. In some embodiments, image light is only directed into one eye of the wearer of head mounted device 100. In an embodiment, both displays 130A and 130B are included to direct image light into waveguides 150A and 150B, respectively.

Figure 2:
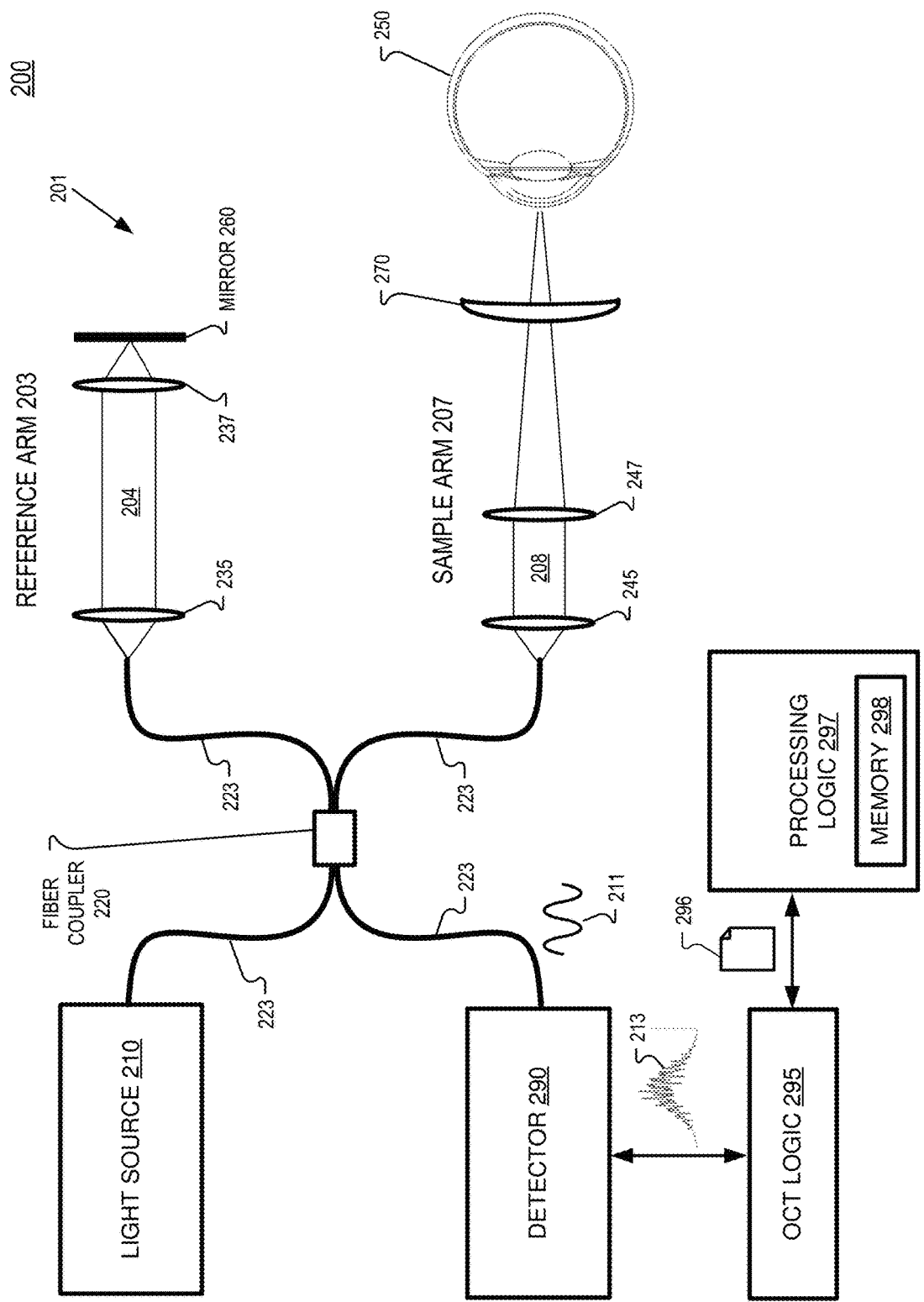
FIG. 2 illustrates an example system that includes an optical coherence tomography (OCT) device that may be utilized to capture volumetric depth images that include prescription lenses and the eyes of a wearer of the prescription lenses, in accordance with aspects of the disclosure.

FIG. 2 illustrates an example system 200 that includes an optical coherence tomography (OCT) device 201 that may be utilized to capture volumetric depth images that include prescription lenses and the eyes of a wearer of the prescription lenses, in accordance with aspects of the disclosure. The illustrated OCT system 200 is a Fourier-domain OCT system rather than a time-domain OCT system. In time-domain OCT systems, a reference mirror of the reference arm is moved axially during the signal acquisition whereas the reference mirror is kept stationary in Fourier-domain OCT systems. Fourier-domain OCT system 200 may be a spectral-domain OCT system or a swept-source OCT system. When system 200 is a spectral-domain OCT system, light source 210 includes a broadband light source and detector 290 includes a spectrometer. When system 200 is a swept-source OCT system, light source 210 includes a swept laser source and detector 290 includes a photodetector OCT system 200 is one example of an imaging system that may capture volumetric depth images that include prescription lenses and the eyes of the wearer of the prescription lenses. A volumetric depth image may be generated by a time-of-flight imaging system, a Light Detection and Ranging (LIDAR) imaging system, or focused ultrasound imaging, in accordance with other embodiments of the disclosure.

System 200 includes OCT device 201 that includes a light source 210, a reference arm 203, a sample arm 207, a fiber coupler 220, a detector 290, and OCT logic 295. System 200 also includes processing logic 297 that includes memory 298. In some embodiments, memory 298 may be external to processing logic 297 and processing logic 297 is configured to read and/or write to the external memory.

OCT device 201 is configured to capture a volumetric depth image 296 that includes imaging of prescription lens 270 and at least a portion of eye 250. In addition to the eye 250 of a wearer of prescription lens 270, the volumetric depth image 296 may also include portions of the face of a wearer of prescription lens 270 such that volumetric depth image 296 captures a three-dimensional image of the prescription lens 270 with respect to the face and/or eye of the wearer of prescription lens 270.

Light source 210 may include a non-visible light source that illuminates optical fiber 223 with illumination light that encounters fiber coupler 220. Non-visible light may be defined as light having wavelengths that are outside the visible light range, such as ultraviolet light and infrared light. In aspects of this disclosure, visible light may be defined as having a wavelength range of approximately 380 nm-700 nm. Infrared light having a wavelength range of approximately 700 nm-1 mm includes near-infrared light. In aspects of this disclosure, near-infrared light may be defined as having a wavelength range of approximately 700 nm-1.4 µm. Using infrared light allows for shallow penetration into a sample such that a depth below skin or eyes may be imaged. In an example spectral-domain OCT embodiment, light source 210 is a broadband light source emitting non-visible illumination light centered around 840 nm. In an example swept-source OCT embodiment, light source 210 is a swept-source laser. Fiber coupler 220 may be a 2×2 fiber coupler that splits the illumination light between the reference arm 203 and sample arm 207. Reference arm 203 may include optical elements 235 and 237 to focus the reference light 204 to reference mirror 260. Sample arm 207 may include optical elements 245 and 247 to focus the sample light 208 to the sample (the prescription lens 270 and eye 250, in the illustrated example). Reference mirror 260 may be positioned at a same or similar optical pathlength as the sample to be imaged.

Backscattered light from the prescription lens 270 and eye 250 or face (not illustrated) interfere at fiber coupler 220 to generate optical interference signal 211 that is received by detector 290. Detector 290 generates an optical spectrum signal 213 from the optical interference signal 211. Surfaces of the sample that backscatter a significant amount of light will cause interferences of greater intensity. In an example spectral-domain OCT embodiment, detector 290 is a 250 kHz spectrometer. In an example swept-source OCT embodiment, detector 290 is a photodiode.

Figure 4:
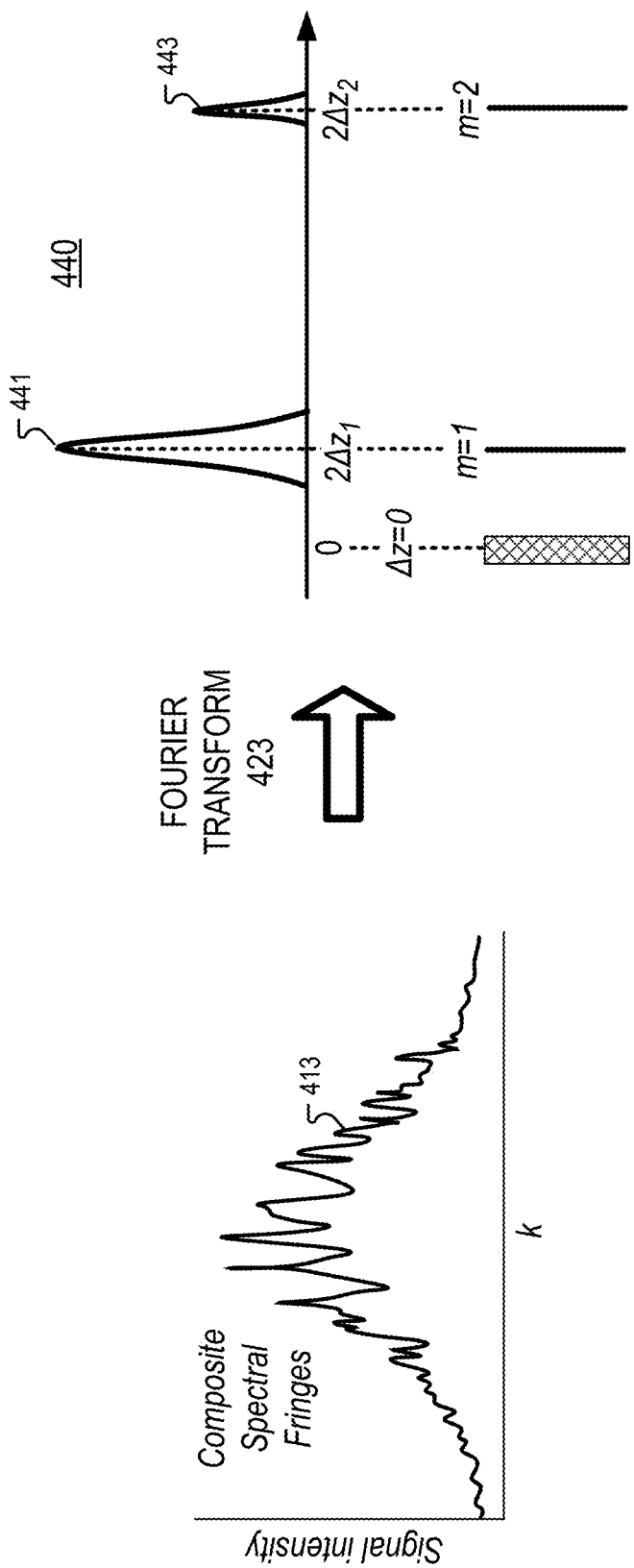
FIG. 4 illustrates a Fourier transform of an optical spectrum signal generating a depth signal, in accordance with aspects of the disclosure.

FIG. 4 illustrates that a Fourier Transform 423 of an optical spectrum signal 413 generates a depth profile 440 and that the peaks 441 and 443 of depth profile 440 are representative of backscattering surfaces of the sample. In FIG. 4, peak 441 may be generated by a backscattering of a first surface of prescription lens 270 and peak 443 may be generated by a backscattering of a second surface of prescription lens 270, for example. Other surfaces of the sample such as the cornea, limbus, iris/pupil, and/or lens may also generate backscattered light that contributes to a depth profile. Thus, a depth profile may be generated from each optical spectrum signal (e.g. 213) generated by an OCT device (e.g. OCT device 201).

Figure 5:
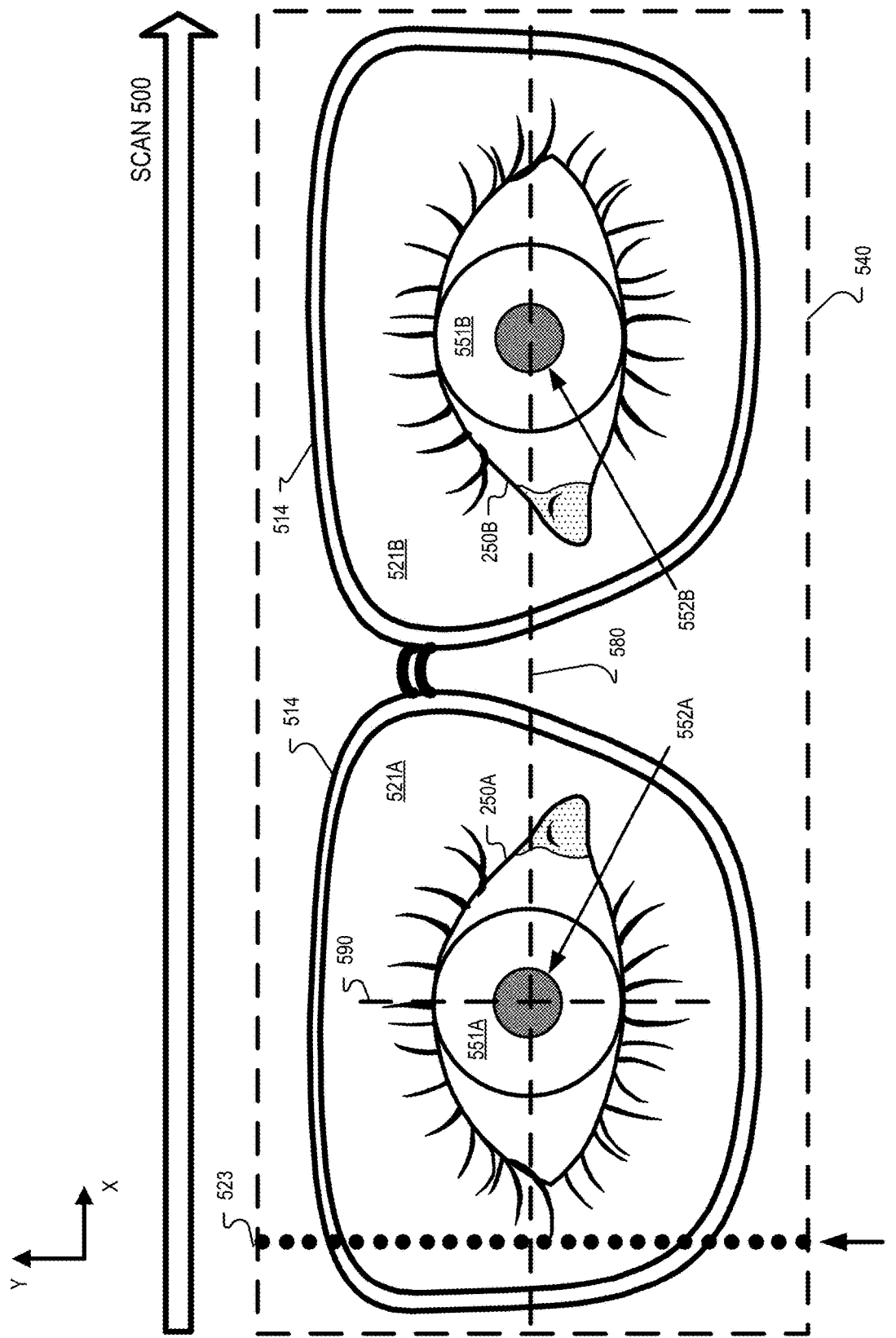
FIG. 5 illustrates an example scan of a person wearing eyeglasses including frames configured to hold prescription lenses in position on the face of a wearer of the prescription lenses, in accordance with aspects of the disclosure.

FIG. 5 illustrates an example scan 500 of a person wearing eyeglasses including frames 514 configured to hold prescription lenses 521A and 521B in position on the face of a wearer of the prescription lenses 521A and 521B. In a scan 500 to acquire a volumetric depth image, a plurality of depth profiles 523 are acquired to generate a volumetric depth image over example scan field 540. Example scan field 540 includes both prescription lenses 521A and 521B and eyes 250A and 250B, although the scan field in some embodiments may be more or less than scan field 540 in FIG. 5. Eyes 250 includes iris 551 and pupil 522, in FIG. 5. Capturing a volumetric depth image may include scanning lines of depth profiles 523 across scan field 540. Example line 521 includes twenty-four depth profiles 523, for example. Some lines (e.g. line 521) may include 250 depth profiles 523 and 500 lines may be captured in a scan 500 going from left to right. Consequently, generating a volumetric depth image (e.g. volumetric depth image 296) may include capturing 125,000 depth profiles 523, in that example. Capturing each depth profile 523 may take approximately 4 µs. Other lateral positions and scan rates may also be utilized. OCT logic 295 may receive an optical spectrum signal 213 for each depth profile 523, perform a Fourier Transform on each received optical spectrum signal 213 to generate a depth profile for each optical spectrum signal and then aggregate the depth profiles to generate a volumetric depth image 296 of the entire scan field. In FIG. 2, the volumetric depth image 296 is provided to processing logic 297 for further processing.

Figure 6A:
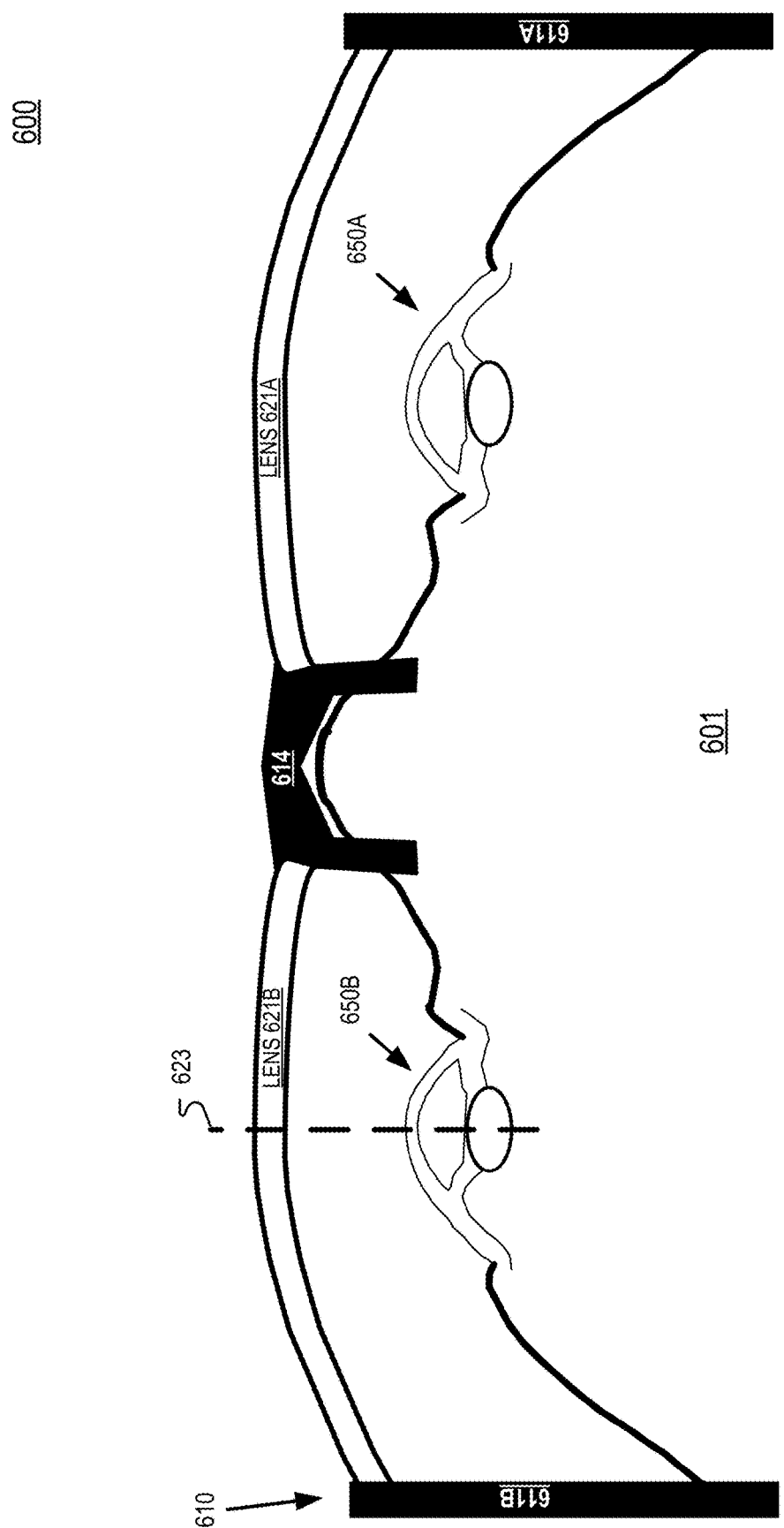
FIGS. 6A-6B illustrate a slice of a volumetric depth image through a horizontal plane, in accordance with aspects of the disclosure.

FIG. 6A illustrates a slice 600 of a volumetric depth image through a horizontal plane indicated by dashed-line 580 of FIG. 5, in accordance with aspects of the disclosure. Slice 600 may be generated by a plurality of depth profiles 623. Slice 600 shows that eyeglasses 610 include arms 611A and 611B attached to glasses frame 614 securing prescription lenses 621A and 621B. Prescription lens 621A corrects the vision of eye 650A of wearer 601 and prescription lens 621B corrects the vision of eye 650B of wearer 601.

Figure 6B:
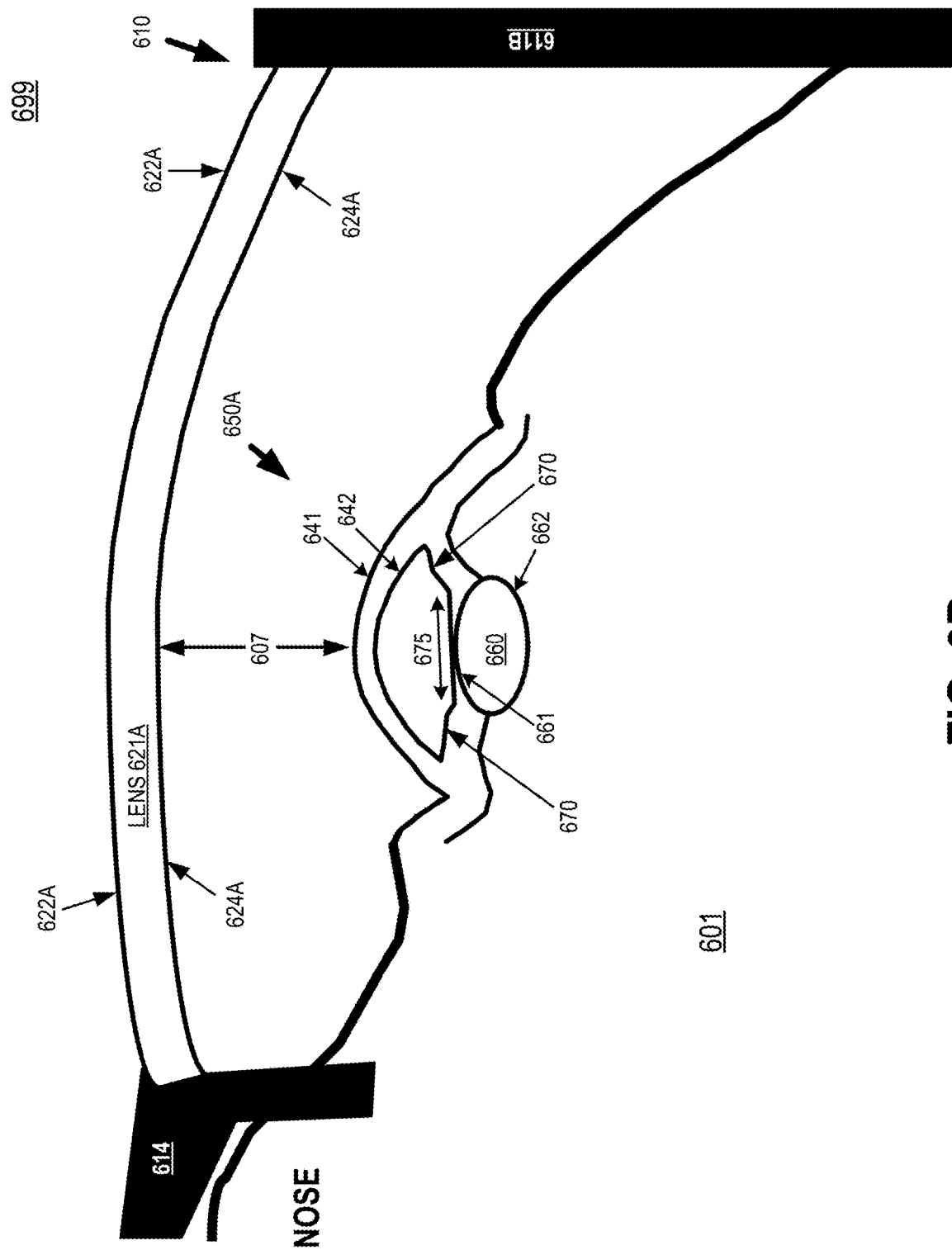

FIG. 6B illustrates a zoomed-in portion 699 of slice 600, in accordance with aspects of the disclosure. Prescription lens 621A of eyeglasses 610 includes a front surface 622A and a back surface 624A. An eye-relief measurement 607 may be determined from a front surface 641 of a cornea of eye 650A and a point on the back surface 624A of lens 621A. The front surface 641 of the cornea, the back surface 642 of the cornea, the front surface 661 of eye lens 660, the back surface 662 of eye lens 660, and iris 670 may also generate backscattered light that is significant enough to be imaged in a volumetric depth image. Other features of eye 650A may also generate backscattered light that can be imaged by an OCT device such as OCT device 201. FIG. 6B illustrates that the skin around the eye and the nose of wearer 601 may also generate backscattered light that can be imaged by an OCT device. The pupil 675 of eye 650A may be determined by the space between iris 670. Although not shown in FIG. 6B, the retina of eye 650A may also be included in the volumetric depth image.

Figure 7:
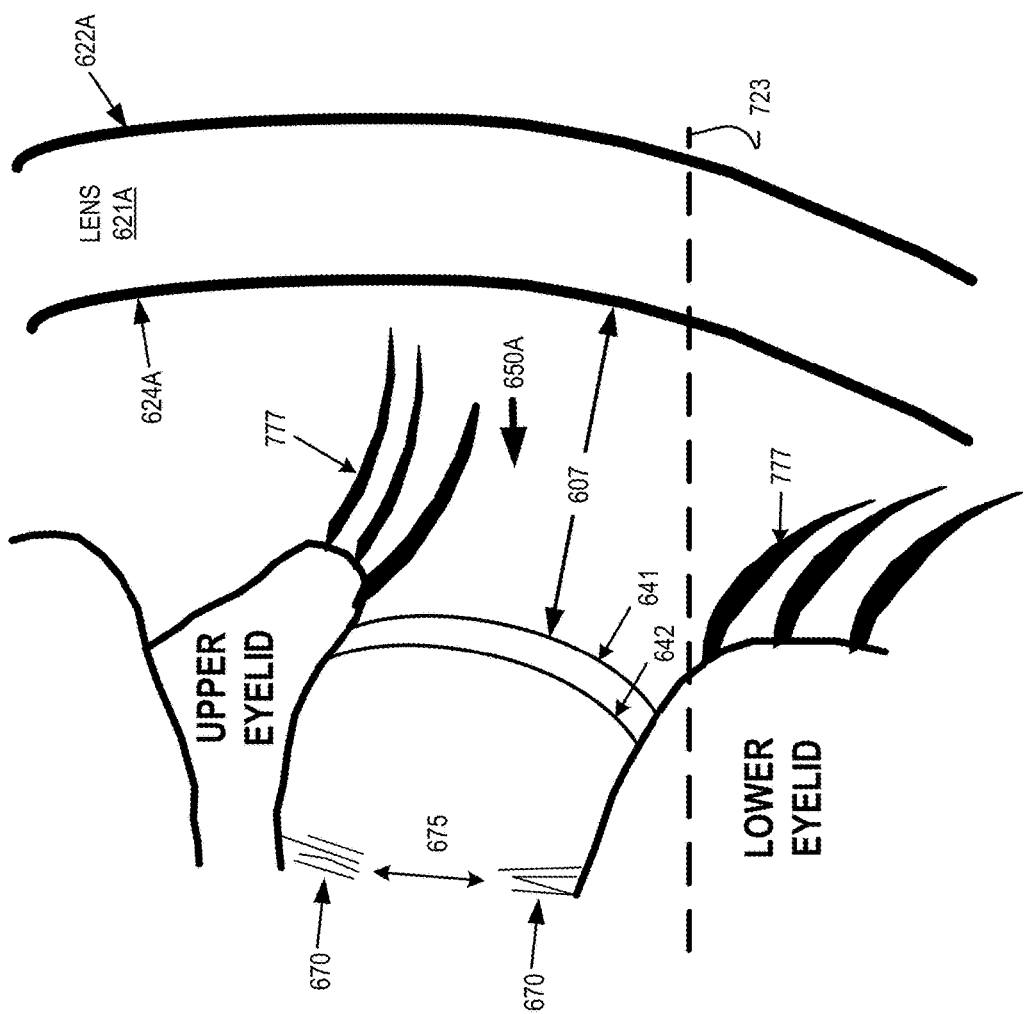
FIG. 7 illustrates a slice of a volumetric depth image through a vertical plane, in accordance with aspects of the disclosure.

FIG. 7 illustrates a slice 700 of a volumetric depth image through a vertical plane indicated by dashed-line 590 of FIG. 5, in accordance with aspects of the disclosure. Slice 700 may be generated by a plurality of depth profiles 723. Slice 700 includes an upper eyelid and a lower eyelid. The volumetric depth image may even include eyelashes 777.

Slice 700 and slice 600 illustrate that a volumetric depth image can include a full three-dimensional image of prescription lenses and the eyes and face of a wearer 601 of eyeglasses 610. Thus, lens-to-eye data that includes measurements of the prescription lens(es) with respect to the eye 650 can be generated. FIGS. 6B and 7 show eye-relief measurement 607 as one example of lens-to-eye data. In addition, a base curve of the front surface 622A and a back curve of back surface 624A of prescription lens 621A may also be generated since lens 621A is fully imaged in three-dimensions in the volumetric depth image. For the purposes of the disclosure, the term "base curve" is associated with the profile of the front surface (e.g. 622A) of a prescription lens and the term "back curve" is associated with the profile of the back surface (e.g. 624A) of the prescription lens.

FIG. 8A illustrates that when both eyes 650A and 650B are included in a volumetric depth image, an interpupillary distance (IPD) 817 can also be derived from the distance between a first pupil 675A of eye 650A and a second pupil 675B of eye 650B. A pupil size (e.g. diameter) of pupils 675 may also be measured from a volumetric depth image.

FIG. 8B illustrates that an eye-relief measurement 807 from a volumetric depth image can be measured from any point of the cornea of the eye to any point on the back surface of lens 821. FIG. 8C illustrates a frame tilt angle 809 from a volumetric depth image can be measured to derive the angle at which glasses frames (not illustrated hold the prescription lens(es) 821 with respect to a vertical plane.

Figure 3A:
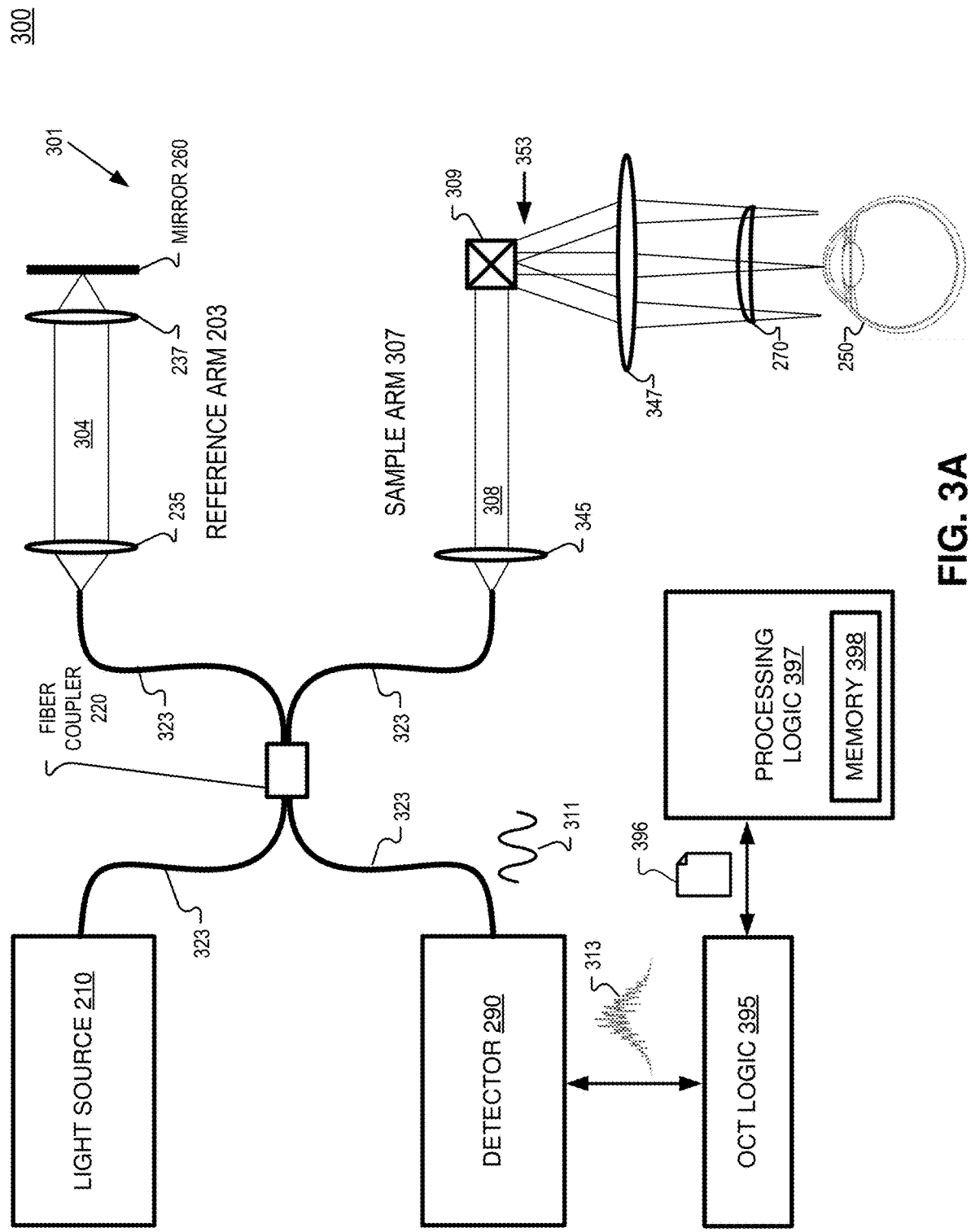
FIGS. 3A-3B illustrate another example system that includes an optical coherence tomography (OCT) device that includes a scanner that may be utilized to capture volumetric depth images that include prescription lenses and the eyes of a wearer of the prescription lenses, in accordance with aspects of the disclosure.

FIG. 3A illustrates another example system 300 that includes an optical coherence tomography (OCT) device 301 that may be utilized to capture volumetric depth images that include prescription lenses and the eyes of a wearer of the prescription lenses, in accordance with aspects of the disclosure. The illustrated OCT system 300 is a Fourier-domain OCT system similar to OCT system 200 where a two-dimensional scanner 309 and a scan or eyepiece lens 347 has been included in sample arm 307. Scanner 309 may be implemented with a micro-electro-mechanical systems (MEMS) micro-mirror to quickly direct light 308 to different regions of a scan field (e.g. scan field 540) of eye 250.

Figure 3B:
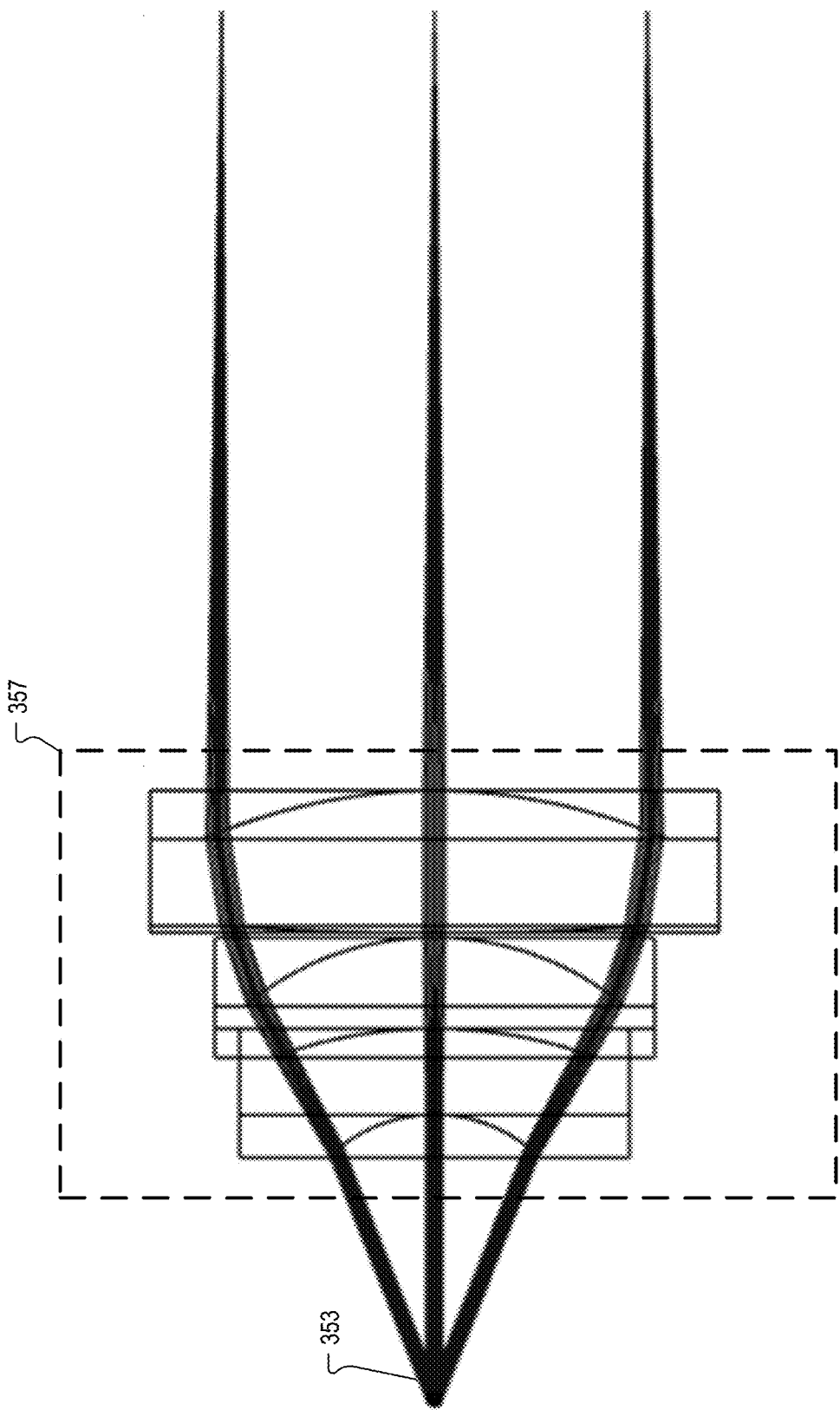

FIG. 3B illustrates an example scan lens 357 configured to distribute light 308 from an exit point 353 of scanner 309 to a particular focus point for a particular depth profile. In other words, scanner 309 may direct light 308 at a variety of angles when capturing different depth profiles 523 to cover the scan field and scan lens 357 is configured to direct the light 308 to the sample and focus backscattered light from the sample back to scanner 309 to be reflected back to fiber coupler 220 via the optical fiber 323.

OCT device 301 is configured to capture a volumetric depth image 396 that includes prescription lens 270 and at least a portion of eye 250. In addition to the eye 250 of a wearer of prescription lens 270, the volumetric depth image 396 may also include portions of the face of a wearer of prescription lens 270 such that volumetric depth image 396 captures a three-dimensional image of the prescription lens 270 with respect to the face and/or eye 250 of the wearer of prescription lens 270. System 300 also includes processing logic 397 that includes memory 398. In some embodiments, memory 398 may be external to processing logic 397 and processing logic 397 is configured to read and/or write to the external memory.

Backscattered light from the prescription lens 270 and eye 250 or face (not illustrated) interfere at fiber coupler 220 to generate optical interference signal 311 that is received by detector 290. Detector 290 generates an optical spectrum signal 313 from the optical interference signal 311. A plurality of optical spectrum signals 313 for a plurality of depth profiles may be aggregated to generate volumetric depth image 396, in FIG. 3A.

Volumetric depth images (e.g. images 296 or 396) provide a dense 3D image of the eye and/or face of a wearer with respect to prescription lenses. This allows for a reconstruction of the prescription surface profile of the prescription lens such that the optical power of the prescription lens, the base curve, and the back curve of the prescription lens can be known.

While FIGS. 2-3B illustrate example embodiments of OCT systems for generating volumetric depth images, other OCT systems may also be deployed to capture volumetric depth images. For example, an OCT system with multiple spectrometers and/or reference arms may be used where different spectrometers and/or reference arms are configured to measure different depths to increase the depth of the volumetric depth image by stitching together images of different imaging depths. An OCT system may also include multiple scan lenses to increase a field of view (FOV) of the OCT system. In some embodiments, multiple scanner pairs of an OCT system are activated in parallel where each of the scanner pairs is configured to image different FOVs of different parts of the face in order to reduce an acquisition time of the volumetric depth image by stitching the different captured FOVs together as one volumetric depth image. An OCT system that includes a single axis (line) galvo scanner may be utilized to increase the acquisition speed of volumetric depth image(s), in some embodiments. In some embodiments, a full-field OCT system may be used.

Figure 9B:
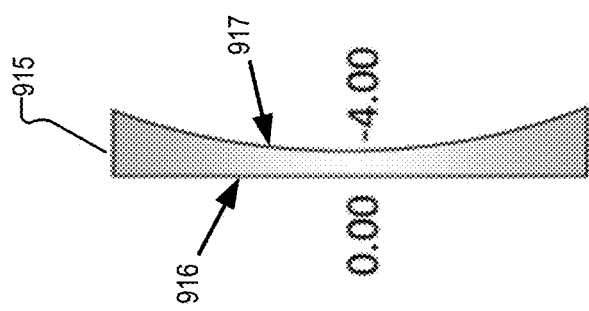
FIGS. 9A-9B illustrate an example meniscus prescription lens and an example plano-concave lens having the same optical power, in accordance with aspects of the disclosure.
Figure 9A:
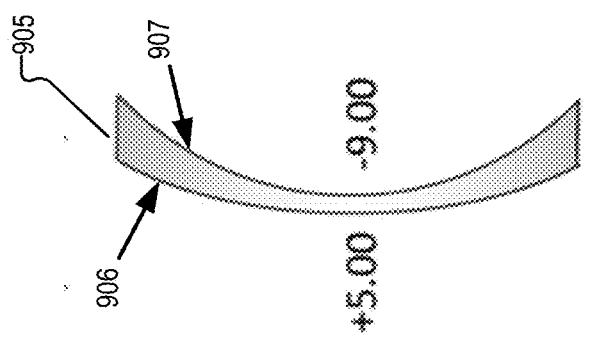

FIG. 9A illustrates an example meniscus prescription lens 905 for eyeglasses having an optical power of −4.00 Diopter where the base curve of the front surface 906 has a +5.00 curve and the back curve of the back surface 907 has a −9.00 curve. FIG. 9B illustrates an example plano-concave lens 915 having the same −4.00 Diopter optical power generated by a plano front surface 916 having a 0.00 curve and a concave back surface 917 having a −4.00 curve. Meniscus prescription lens 905 is commonly used in prescription lenses for conventional eyeglasses while plano-concave lens 915 may be utilized for use in a head mounted device that includes a prescription lens so that the plano front surface 916 of plano-concave lens 915 can be bonded to a planar surface of additional optical layers (e.g. eye-tracking layer and/or display layer) of a head mounted device such as an AR head mounted display (HMD). Yet, although lens 905 and 915 have the same optical power, users may experience discomfort during a transition time between switching between lens 905 and 915. The transition time may be attributed to distortion changes in the lens itself, residual aberrations, or a fitting mismatch. The residual aberrations may be attributed to uncorrected lower and higher order aberrations in the lenses and the fitting mismatch may be attributed to a decentration of the lenses (housed in glasses) on the wearer's face that may result in unwanted distortion or image shift.

Thus, having volumetric depth images that provide a dense 3D image of the eye or face of a wearer with respect to prescription lenses may allow a three-dimensional (3D) optical-mechanical fit profile to be generated for a wearer of glasses and the 3D optical-mechanical fit profile can be used to adjust a configuration of a head mounted device specifically for the wearer, based on a volumetric depth image of the wearer wearing their prescription lenses of their eyeglasses. The adjustment to the head mounted device based on the 3D optical-mechanical fit profile may assist in reducing or eliminating a transition time between a wearer's conventional prescription eyeglasses and a head mounted device that includes corrective lenses.

Figure 10:
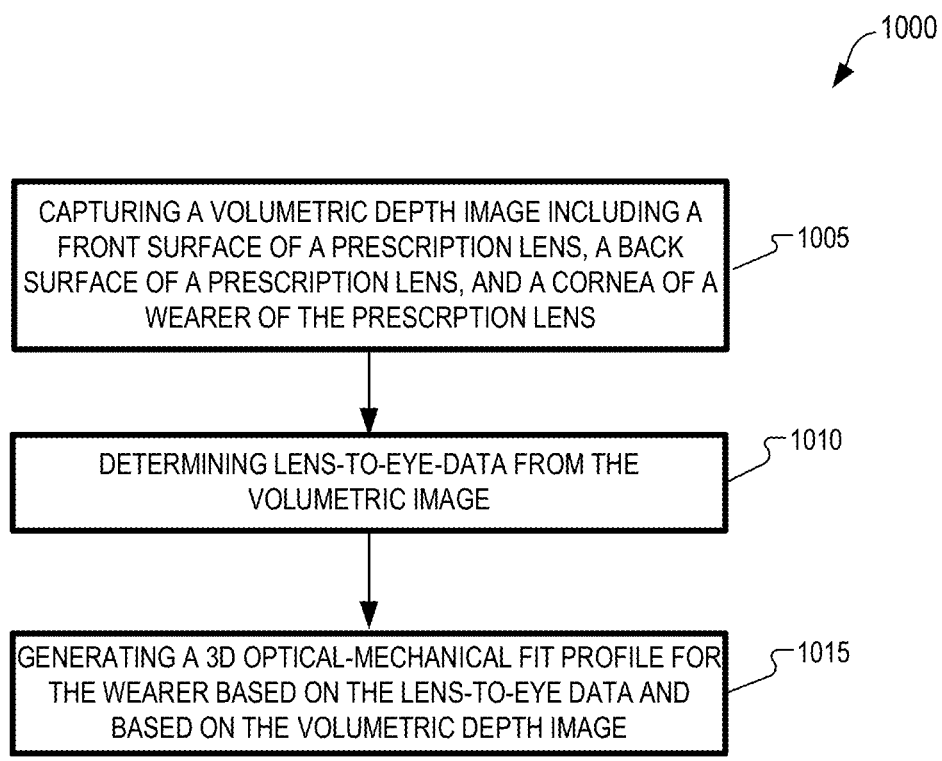
FIG. 10 illustrates a process of generating a 3D optical-mechanical fit profile for a user from a volumetric depth image of the wearer wearing their prescription eyeglasses, in accordance with aspects of the disclosure.

FIG. 10 illustrates a process 1000 of generating 3D optical-mechanical fit profile for a user from a volumetric depth image of the wearer wearing their prescription eyeglasses, in accordance with an embodiment of the disclosure. The order in which some or all of the process blocks appear in process 1000 should not be deemed limiting. Rather, one of ordinary skill in the art having the benefit of the present disclosure will understand that some of the process blocks may be executed in a variety of orders not illustrated, or even in parallel.

In process block 1005, a volumetric depth image (e.g. volumetric depth image 296 or 396) is captured. The volumetric depth image includes a front surface of a prescription lens, a back surface of the prescription lens, and a cornea of an eye of a wearer of the prescription lens. The volumetric depth image may also include a limbus, an iris/pupil definition, a retina mapping, a definition of an anterior chamber of the eye, and/or a lens of the eye of the wearer of the prescription lens. In an embodiment, the volumetric depth image also includes a second prescription lens and a second eye of the wearer of the second prescription lens.

In process block 1010, lens-to-eye data is determined from the volumetric depth image. The lens-to-eye data includes measurements of the prescription lens with respect to the eye of the wearer. The lens-to-eye data may include a base curve of the front surface (e.g. 622A) of the prescription lens and a back curve of the back surface (e.g. 624A) of the prescription lens. The lens-to-eye data may include an eye-relief measurement. The lens-to-eye data may include an interpupillary distance (IPD) between a first pupil of a first eye and a second pupil of a second eye, when the volumetric depth image includes two eyes. The lens-to-eye data may include at least one of eye-relief distance, pupil size of one or both eyes, frame tilt angle, frame fitting height, or corneal topography of the cornea of one or both eyes. The eye-relief distance may be defined from the back surface of the prescription lens to the cornea of the eye. The frame tilt angle may measure an angle of a glasses frame that holds the prescription lens with respect to a vertical plane.

In process block 1015, a three-dimensional (3D) optical-mechanical fit profile is generated for the wearer based on the lens-to-eye data and based on the volumetric depth image. Therefore, the 3D optical-mechanical fit profile may include a 3D model of the prescription lenses with respect to the eye and/or face of a user and relevant lens-to-eye data. The 3D optical-mechanical fit profile for a particular user may be used to determine a compatibility with a particular head mounted device for a user. For example, an IPD of a user may determine a size of a head mounted device that would be most compatible with the user. The 3D optical-mechanical fit profile for a particular user may be used to adjust a configuration of a head mounted device for a user to reduce or eliminate a transition period between using eyeglasses and a head mounted device that includes corrective lenses specific to the user.

In embodiments of process 1000, capturing the volumetric depth image includes capturing a plurality of optical spectrum signals with an optical coherence tomography (OCT) system (e.g. system 200 or 300) where the optical spectrum signals in the plurality are generated by backscattered light from the front surface of the prescription lens, the back surface of the prescription lens, and the cornea of the eye. The OCT system may be a Fourier-domain OCT system including a light source to illuminate the eye, the prescription lens, and a reference mirror of the Fourier-domain OCT system. The volumetric depth image is generated by performing a Fourier Transform of each of the optical spectrum signals to generate depth profiles that are aggregated together as the volumetric depth image, in some embodiments.

In some embodiments of process 1000, the volumetric depth image is generated by one of time-of-flight imaging, Light Detection and Ranging (LIDAR) imaging, or focused ultrasound imaging.

Figure 11:
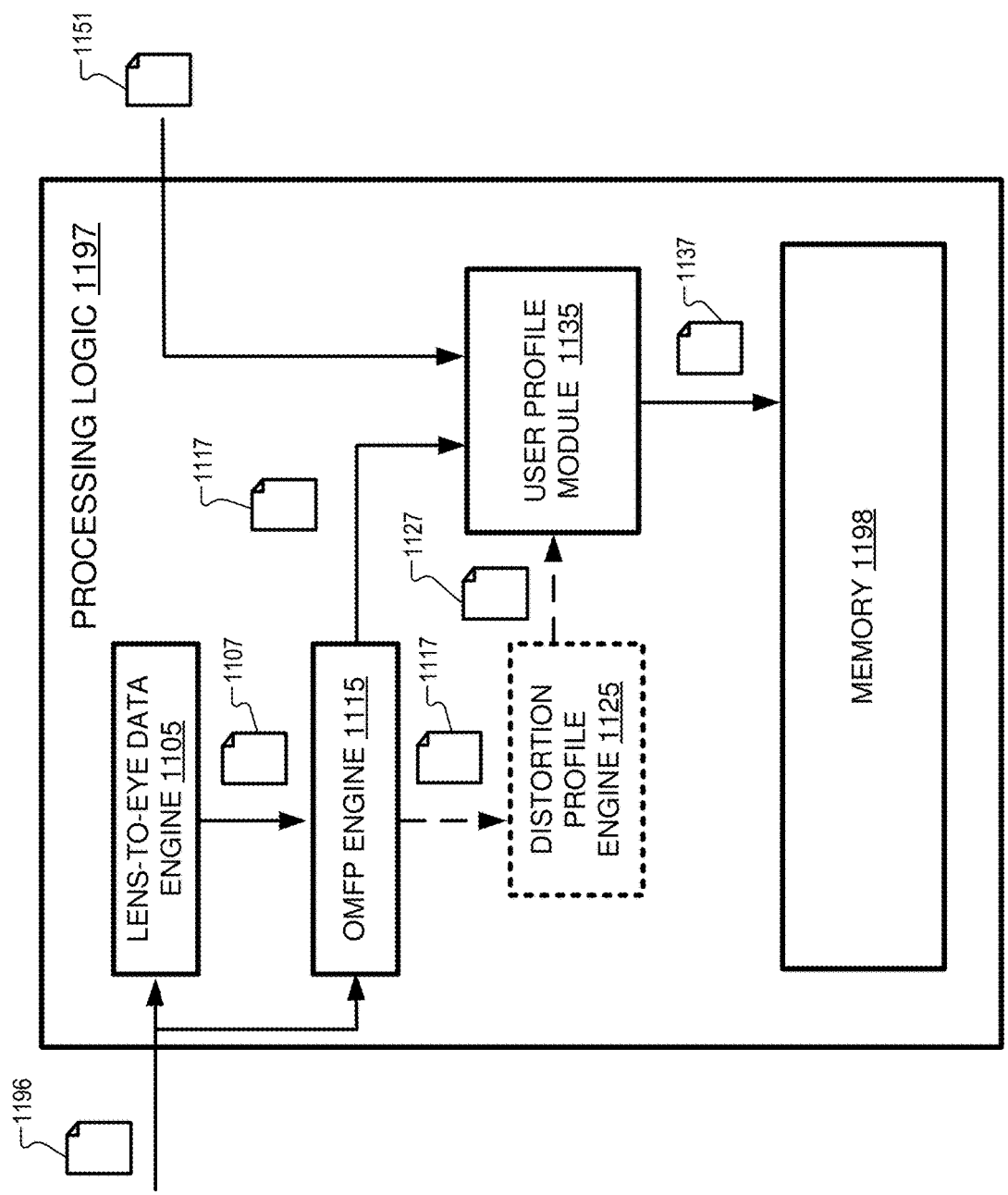
FIG. 11 illustrates example processing logic that may be utilized to execute the process of FIG. 10, in accordance with aspects of the disclosure.

Processing logic 297 or processing logic 397 may be configured to execute process 1000. FIG. 11 illustrates example processing logic 1197 that may be utilized as processing logic 297 or 397 to execute process 1000, in accordance with aspects of the disclosure. Processing logic 1197 includes lens-to-eye data engine 1105, optical-mechanical fit profile engine 1115, distortion profile engine 1125, and user profile module 1135. Processing logic 1197 also includes memory 1198. In some embodiments, memory 1198 may be external to processing logic 1197 and processing logic 1197 is configured to read and/or write to the external memory.

Lens-to-eye data engine 1105 of processing logic 1197 is configured to receive a volumetric depth image 1196. Lens-to-eye data engine 1105 is configured to determine lens-to-eye data 1107 from volumetric depth image 1196. The lens-to-eye data 1107 includes measurements of the prescription lens with respect to the eye of the wearer. The lens-to-eye data 1107 may include a base curve of the front surface (e.g. 622A) of the prescription lens and a back curve of the back surface (e.g. 624A) of the prescription lens. The lens-to-eye data 1107 may include an eye-relief measurement. The lens-to-eye data 1107 may include an interpupillary distance (IPD) between a first pupil of a first eye and a second pupil of a second eye, when the volumetric depth image includes two eyes. The lens-to-eye data 1107 may include at least one of eye-relief distance, pupil size of one or both eyes, frame tilt angle, or corneal topography of the cornea of one or both eyes. Lens-to-eye data engine 1105 may use conventional image processing techniques to determine the lens-to-eye data 1107 such as comparing features in the volumetric depth image 1196 to a size of the image that is known or an object in the volumetric depth image 1196 that has a known size.

Optical-mechanical fit profile engine 1115 is configured to receive volumetric depth image 1196 and lens-to-eye data 1107 and generate 3D optical-mechanical fit profile 1117 based on lens-to-eye data 1107 and volumetric depth image 1196. Optical-mechanical fit profile engine 1115 may be configured to augment volumetric depth image 1196 with lens-to-eye data 1107 to generate 3D optical-mechanical fit profile 1117, in some embodiments.

User profile module 1135 is configured to receive user data 1151 that is associated with volumetric depth image 1196. User data 1151 may include the name or username for the person that was imaged wearing their prescription lenses to generate volumetric depth image 1196. User profile module 1135 may link 3D optical-mechanical fit profile 1117 with user data 1151 to generate user optical profile 1137. User optical profile 1137 may then be stored to memory 1198, uploaded to a cloud database, or provided to a network or another device. User optical profile 1137 may be encrypted for privacy protection.

Distortion profile engine 1125 is optionally included in processing logic 1197 and may be configured to receive 3D optical-mechanical fit profile 1117. Distortion profile engine 1125 may be configured to generate a distortion profile 1127 from 3D optical-mechanical fit profile 1117. Distortion profile engine 1125 may determine a visual acuity of a prospective user's eye when utilizing a prescription lens of 3D optical-mechanical fit profile 1117 or a Modulation Transfer Function (MTF) and/or a point spread function (PSF) of the prescription lens(es) of 3D optical-mechanical fit profile 1117, in some embodiments, and include that MTF and/or PSF in distortion profile 1127. The MTF and/or PSF may be determined from the prescription lenses imaged in volumetric depth image 1196. It may be advantageous to fabricate a plano-concave lens (e.g. 915) for a head mounted device that includes similar see-through optical performance of the existing prescription lenses to reduce or eliminate a transition period between switching between eyeglasses and the head mounted device. Thus, the plano-concave lens may be fabricated with the same or similar distortion profile as the user's existing prescription lenses, as measured by visual acuity, MTF and/or PSF. The same or similar distortion profile may be designed for the plano-concave lens by optical design software in order to match the distortion profile of the existing prescription lenses.

When distortion profile engine 1125 is included in processing logic 1197, distortion profile 1127 may be provided to user profile module 1135 and user profile module 1135 may link distortion profile 1127 with user data 1151 to generate user optical profile 1137. User optical profile 1137 may then be stored to memory 1198, uploaded to a cloud database, or provided to a network or another device. In this embodiment, distortion profile 1127 may include the data of 3D optical-mechanical fit profile 1117.

Figure 12:
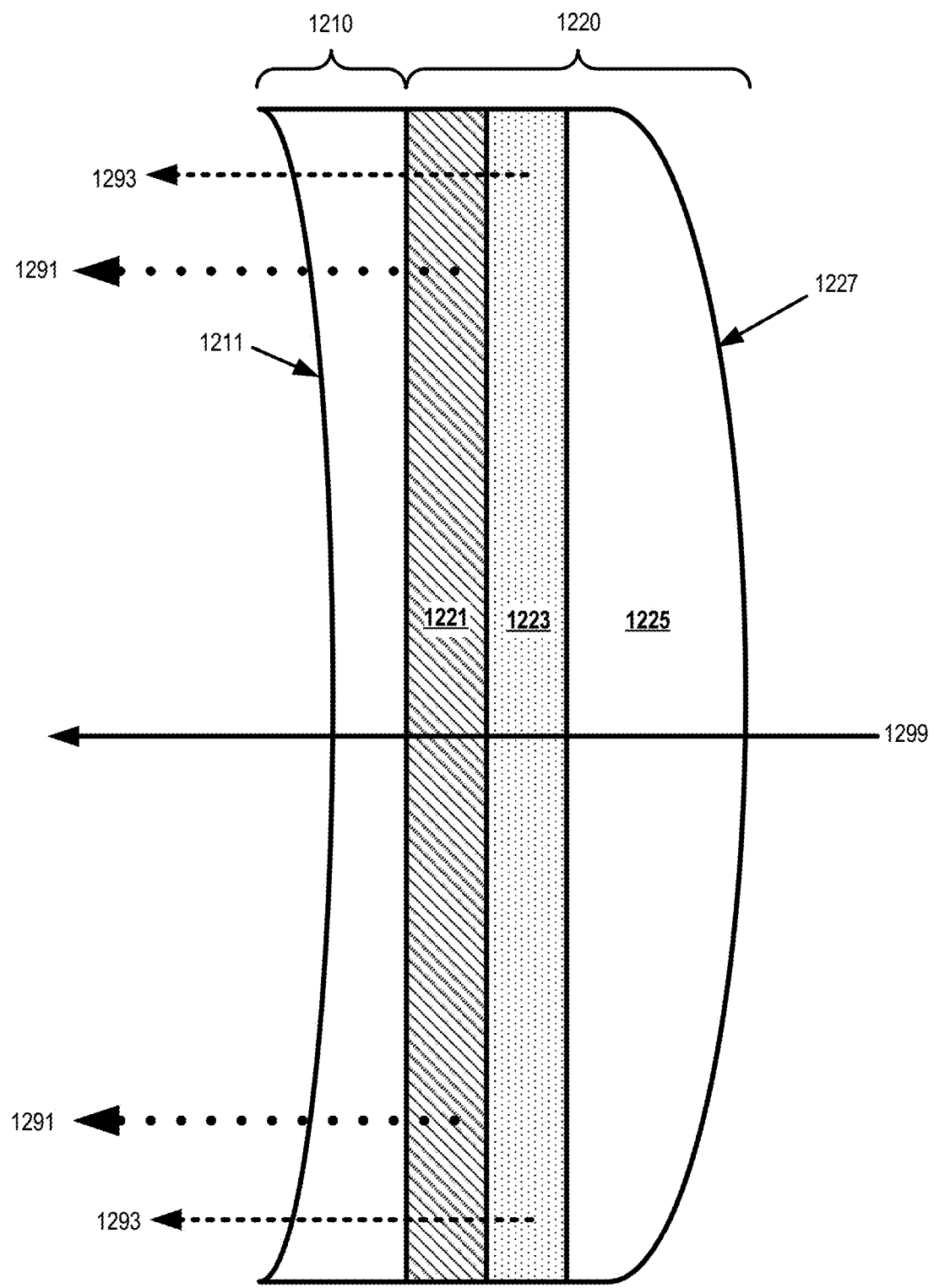
FIG. 12 illustrates an example prescription optical element for a head mounted display that includes a plano-concave optical layer and an optical element, in accordance with aspects of the disclosure.

FIG. 12 illustrates an example prescription optical element 1200 for a head mounted device that includes a plano-concave optical layer 1210 and an optical element 1220, in accordance with aspects of the disclosure. Example prescription optical element 1200 may be used as a corrective lens in a head mounted device such as head mounted device 100. Example optical element 1220 includes an eye-tracking layer 1221, a display layer 1223, and base curve layer 1225. Base curve layer 1225 and plano-concave optical layer 1210 are refractive elements, in FIG. 12. Display layer 1223 directs display light 1293 to an eyebox area to present images to an eyebox area so that an eye of a user can view images included in display light 1293. Display layer 1223 is disposed between base curve 1227 and plano-concave optical layer 1210. Eye-tracking layer 1221 may illuminate the eyebox area with non-visible light 1291 (e.g. infrared light) emitted from an illumination layer for eye-tracking purposes. In some embodiments, eye-tracking layer 1221 may also include a combiner layer to receive reflections of the non-visible light from the eyebox area and redirect the reflections to a camera for imaging the eyebox area. Base curve layer 1225 includes a base curve 1227 and plano-concave optical layer 1210 includes concave-side 1211. The curvature of concave-side 1211 and base curve 1227 provide the optical power for prescription optical element 1200 for real-world scene light 1299 that propagates through prescription optical element 1200.

Figure 13A:
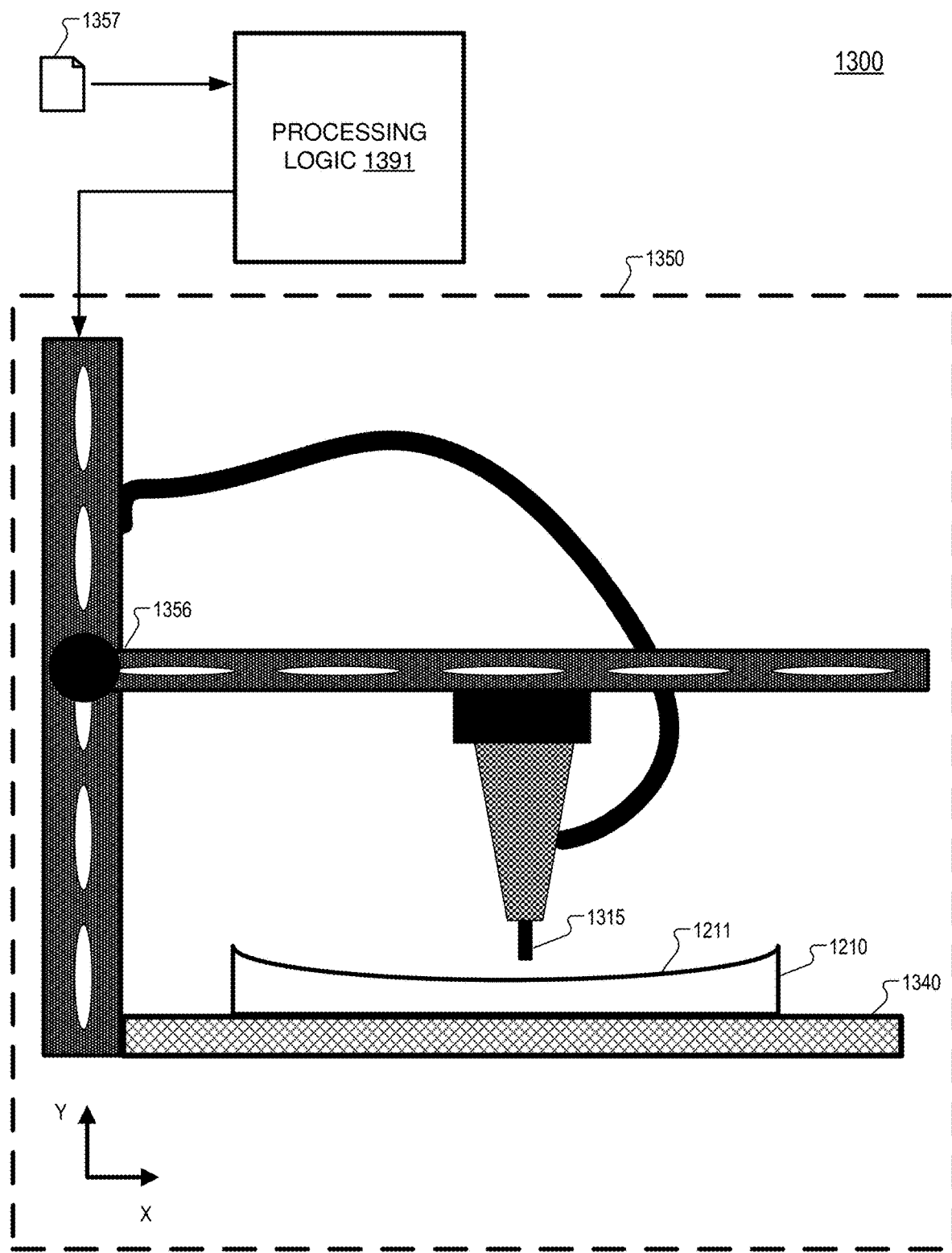
FIGS. 13A-13C illustrates a system for fabricating a plano-concave optical layer based on an optical-mechanical fit profile, in accordance with aspects of the disclosure.

FIG. 13A illustrates a system 1300 for fabricating a plano-concave optical layer based on an optical-mechanical fit profile, in accordance with aspects of the disclosure. System 1300 includes processing logic 1391 and lens shaping apparatus 1350. Lens shaping apparatus 1350 is configured to fabricate plano-concave optical layer 1210 on platform 1340. The illustrated lens shaping apparatus 1350 is configured as a 3D printer that fabricates plano-concave optical layer 1210 in an additive fabrication process by building up plano-concave optical layer 1210 with a 3D printing material such as resin provided through nozzle 1315. The resin may be optical resin that is transparent. Lens shaping apparatus 1350 includes a stage 1356 for moving nozzle 1315 in three dimensions.

Processing logic 1391 is configured to receive optical-mechanical fit profile 1357. User optical profile 1137 may be provided to processing logic 1391 as optical-mechanical fit profile 1357. Optical-mechanical fit profile 1357 may be received from a cloud database in some embodiments. Optical-mechanical fit profile 1357 may include a mapping of prescription lenses with respect to a face of a wearer of the prescription lenses. Optical-mechanical fit profile 1357 may include an interpupillary distance (IPD) between a first pupil of a first eye of the wearer and a second pupil of a second eye of the wearer of the prescription lenses. Optical-mechanical fit profile 1357 may include a distortion profile and an optical power of the prescription lenses. Processing logic 1391 is coupled to drive lens shaping apparatus 1350 to fabricate plano-concave optical layer 1210 based on optical-mechanical fit profile 1357. Plano-concave optical layer 1210 may then be coupled to optical element 1220 to form prescription optical element 1200 for a head mounted device.

As discussed briefly above, a base curve 1227 of optical element 1220 may be different from a base curve of prescription lenses (e.g. base curve of front surface 906) worn by a user in conventional eyeglasses. The curvature of concave-side 1211 of plano-concave optical layer 1210 and the base curve 1227 combine to provide the same optical power as the user's conventional prescription lenses so that scene light from the user's ambient environment will be focused for their eye(s). Base curve 1227 may have a nominal base curve of +0.5 Diopters, in one example. Other base curves may also be used. Additionally, plano-concave optical layer 1210 may be fabricated so prescription optical element 1200 has a matched distortion profile that is substantially similar to the distortion profile of the conventional prescription lenses worn by the user to reduce an adaptation time of switching between the conventional prescription lenses and the head mounted device that includes prescription optical element 1200. The head mounted device is an AR HMD, in some embodiments. Plano-concave optical layer 1210 may also be fabricated so two prescription optical elements 1200 have the same IPD as the user's eyeglasses, when taking into account where the two prescription optical elements will be situated within a frame (e.g. 114) of a head mounted device.

The distortion profile of the prescription lenses may be the visual acuity, MTF, and/or PSF of the prescription lenses that are then matched to the prescription optical element 1200. The see-through optical properties of display layer 1223 (if included in prescription optical element 1200) and/or the see-through optical properties of eye-tracking layer 1221 (if included in prescription optical element 1200) may be accounted for when fabricating plano-concave optical layer 1210 such that prescription optical element 1200 has a matched distortion profile that is substantially similar to the distortion profile of the conventional prescription lenses in the eyeglasses worn by the user.

Figure 13B:
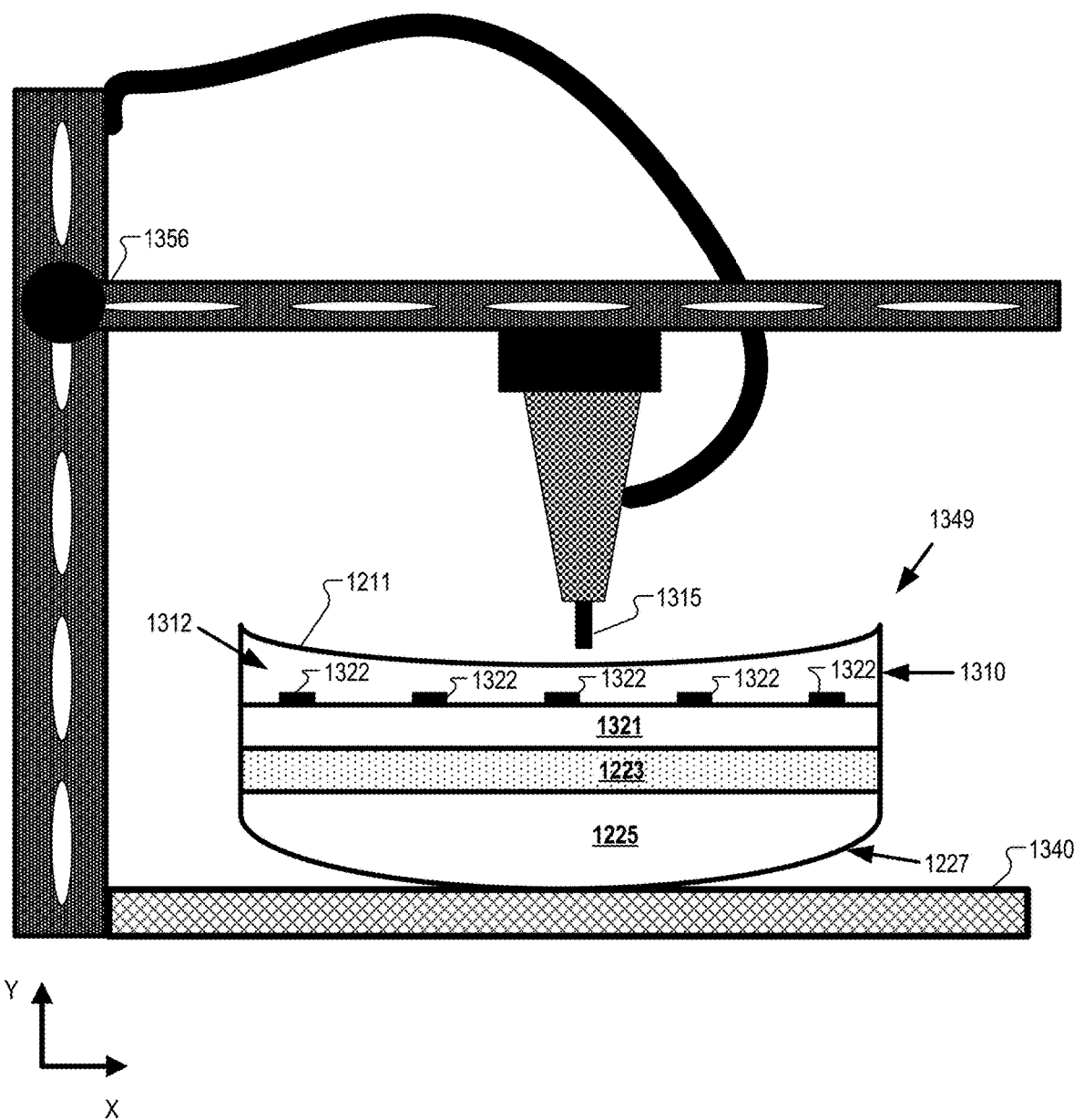

FIG. 13B illustrates an embodiment where optical resin 1312 encapsulates infrared illuminators 1322 of illumination layer 1321, in accordance with aspects of the disclosure. Infrared illuminators 1322 may include an array of infrared light emitting diodes (LEDs) or an array of infrared vertical-cavity surface emitting lasers (VCSELs) configured to illuminate an eyebox area with infrared light. Fabricating plano-concave optical layer 1310 by encapsulating infrared illuminators 1322 may eliminate additional process steps in fabricating a prescription optical element 1349 because 3D printing plano-concave optical layer 1310 onto illumination layer 1321 may eliminate a separate encapsulation process and a bonding process that bonds a plano-concave optical layer (e.g. 1210) to an optical element such as optical element 1220.

Figure 13C:
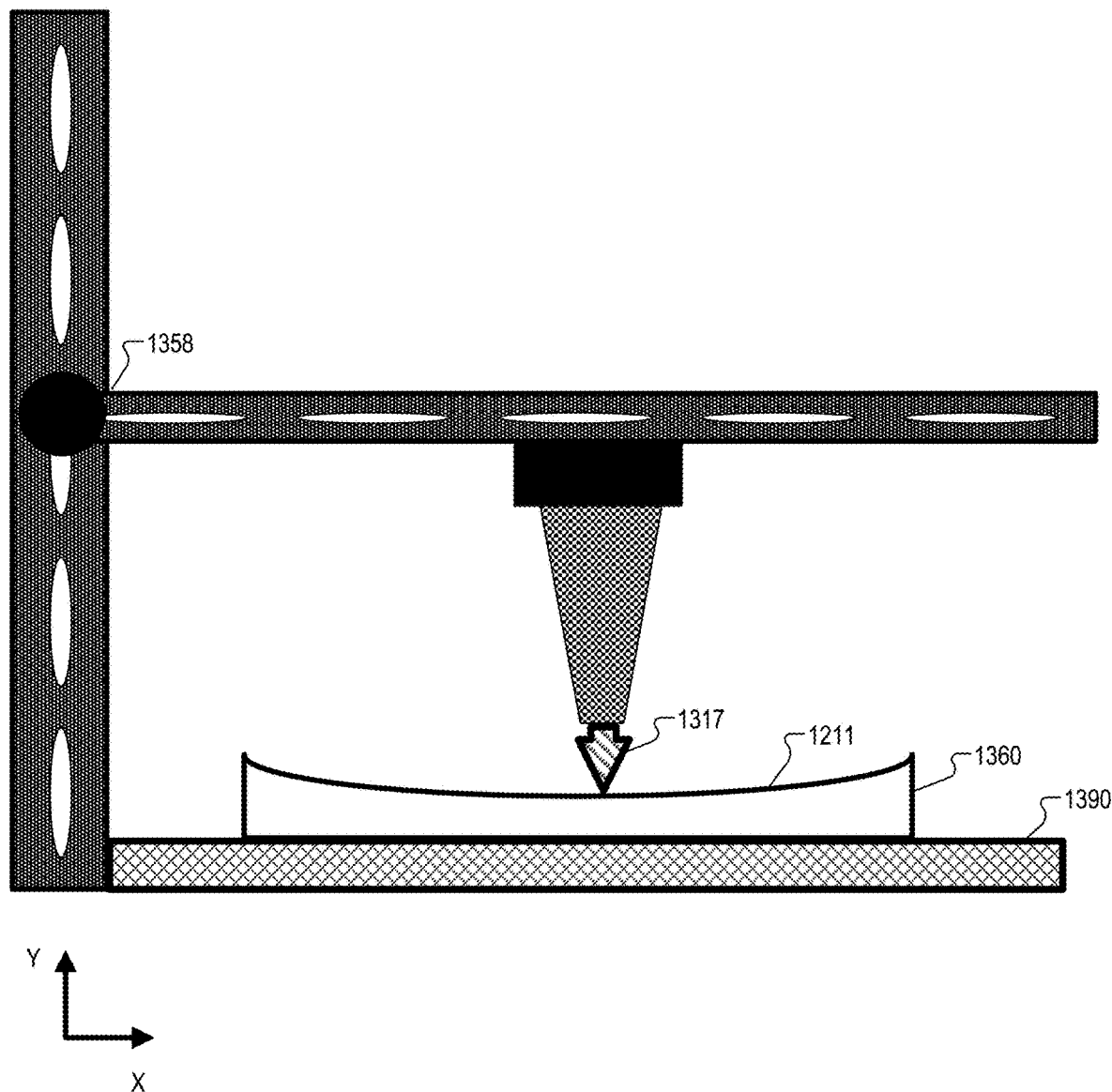

FIG. 13C illustrates a lens shaping apparatus 1351 that may be utilized in place of lens shaping apparatus 1350 to generate a plano-concave optical layer, in accordance with aspects of the disclosure. Lens shaping apparatus 1351 includes a bit 1317 to fabricate plano-concave optical layer 1360 held by platform 1390 using a subtractive fabrication process. Plano-concave optical layer 1360 may be milled from an optical quality refractive material. Lens shaping apparatus 1351 includes a stage 1358 for moving bit 1317 in three dimensions. Lens shaping apparatus 1351 may be configured to facilitate a diamond turning fabrication process, in some embodiments. A plano-concave optical layer may also be fabricated utilizing a casting or molding process (not illustrated).

Figure 14:
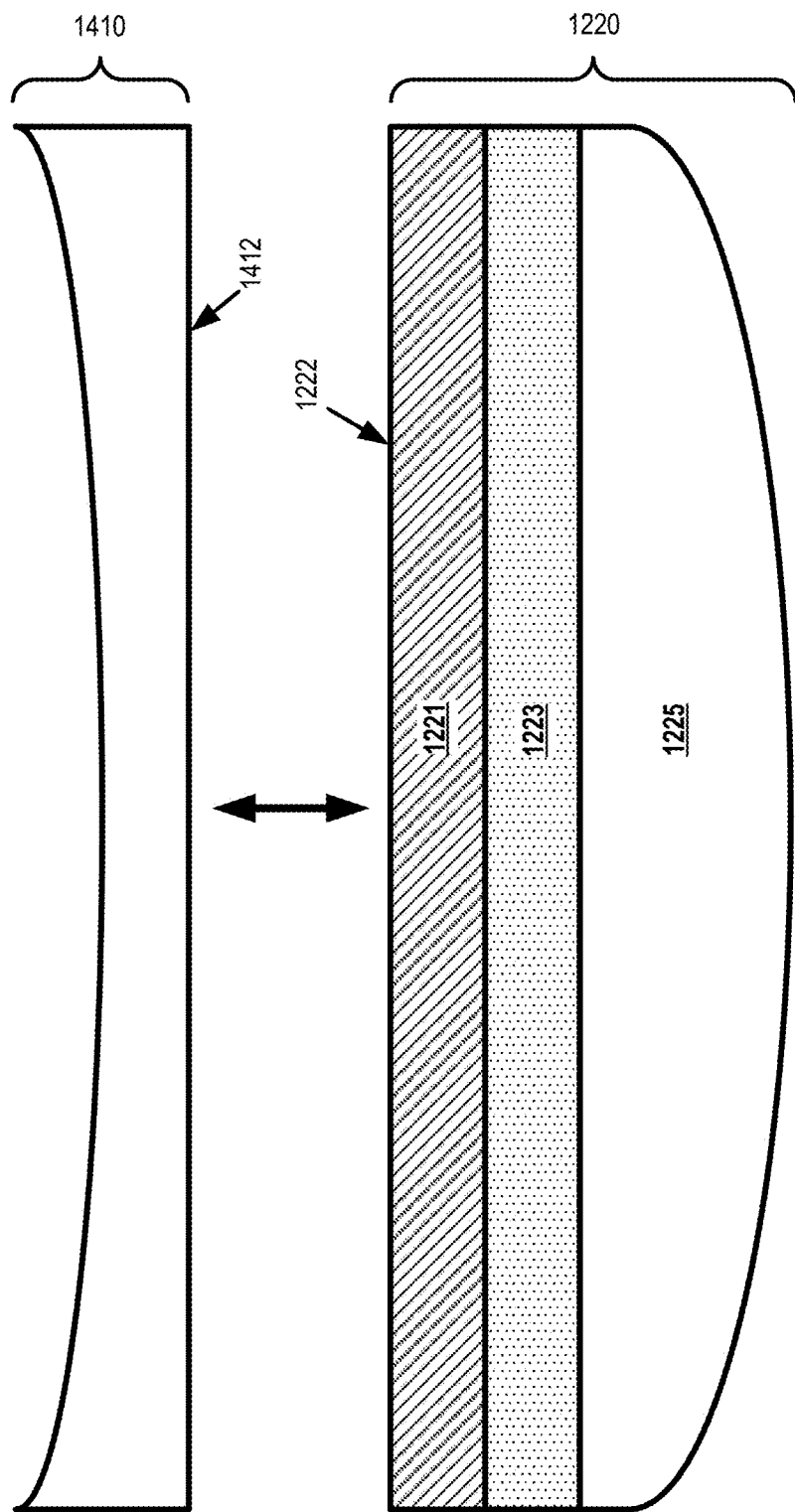
FIG. 14 illustrates a bonding process of fabricating a prescription optical element, in accordance with aspects of the disclosure.

FIG. 14 illustrates a bonding process of fabricating a prescription optical element, in accordance with aspects of the disclosure. In FIG. 14, a plano-side 1412 of plano-concave optical layer 1410 is bonded to a planar surface of eye-tracking layer 1221 of optical element 1220.

Embodiments of the invention may include or be implemented in conjunction with an artificial reality system. Artificial reality is a form of reality that has been adjusted in some manner before presentation to a user, which may include, e.g., a virtual reality (VR), an augmented reality (AR), a mixed reality (MR), a hybrid reality, or some combination and/or derivatives thereof. Artificial reality content may include completely generated content or generated content combined with captured (e.g., real-world) content. The artificial reality content may include video, audio, haptic feedback, or some combination thereof, and any of which may be presented in a single channel or in multiple channels (such as stereo video that produces a three-dimensional effect to the viewer). Additionally, in some embodiments, artificial reality may also be associated with applications, products, accessories, services, or some combination thereof, that are used to, e.g., create content in an artificial reality and/or are otherwise used in (e.g., perform activities in) an artificial reality. The artificial reality system that provides the artificial reality content may be implemented on various platforms, including a head-mounted display (HMD) connected to a host computer system, a standalone HMD, a mobile device or computing system, or any other hardware platform capable of providing artificial reality content to one or more viewers.

The term "processing logic" (e.g. 297, 397, 1197, and/or 1391) in this disclosure may include one or more processors, microprocessors, multi-core processors, Application-specific integrated circuits (ASIC), and/or Field Programmable Gate Arrays (FPGAs) to execute operations disclosed herein. In some embodiments, memories (not illustrated) are integrated into the processing logic to store instructions to execute operations and/or store data. Processing logic may also include analog or digital circuitry to perform the operations in accordance with embodiments of the disclosure.

A "memory" or "memories" (e.g. 298, 398 and/or 1198) described in this disclosure may include one or more volatile or non-volatile memory architectures. The "memory" or "memories" may be removable and non-removable media implemented in any method or technology for storage of information such as computer-readable instructions, data structures, program modules, or other data. Example memory technologies may include RAM, ROM, EEPROM, flash memory, CD-ROM, digital versatile disks (DVD), high-definition multimedia/data storage disks, or other optical storage, magnetic cassettes, magnetic tape, magnetic disk storage or other magnetic storage devices, or any other non-transmission medium that can be used to store information for access by a computing device.

A network may include any network or network system such as, but not limited to, the following: a peer-to-peer network; a Local Area Network (LAN); a Wide Area Network (WAN); a public network, such as the Internet; a private network; a cellular network; a wireless network; a wired network; a wireless and wired combination network; and a satellite network.

Communication channels may include or be routed through one or more wired or wireless communication utilizing IEEE 802.11 protocols, BlueTooth, SPI (Serial Peripheral Interface), I$^2$C (Inter-Integrated Circuit), USB (Universal Serial Port), CAN (Controller Area Network), cellular data protocols (e.g. 3G, 4G, LTE, 5G), optical communication networks, Internet Service Providers (ISPs), a peer-to-peer network, a Local Area Network (LAN), a Wide Area Network (WAN), a public network (e.g. "the Internet"), a private network, a satellite network, or otherwise.

A computing device may include a desktop computer, a laptop computer, a tablet, a phablet, a smartphone, a feature phone, a server computer, or otherwise. A server computer may be located remotely in a data center or be stored locally.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible non-transitory machine-readable storage medium includes any mechanism that provides (i.e., stores) information in a form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A method comprising:
    capturing a volumetric depth image, wherein the volumetric depth image includes a front surface of a prescription lens, a back surface of the prescription lens, and a cornea of an eye of a wearer of the prescription lens;
    determining lens-to-eye data from the volumetric depth image, wherein the lens-to-eye data includes measurements of the prescription lens with respect to the eye;
    generating a three-dimensional (3D) optical-mechanical fit profile for the wearer based on the lens-to-eye data;
    generating a distortion profile based at least in part on a modulation transfer function (MTF) and/or a point spread function (PSF) of the prescription lens of the 3D optical-mechanical fit profile; and
    fabricating a layer of a plano-concave lens to couple with an element of a head mounted display (HMD) to substantially replicate a distortion of an existing prescription lens of the wearer for reducing a period of adjustment to the HMD.

2. The method of claim 1, wherein the lens-to-eye data includes a base curve of the front surface of the prescription lens and a back curve of the back surface of the prescription lens.

3. The method of claim 1, wherein the lens-to-eye data includes an eye-relief measurement.

4. The method of claim 1, wherein the volumetric depth image includes a second prescription lens and a second eye of the wearer of the second prescription lens, and wherein the lens-to-eye data includes an interpupillary distance (IPD) between a first pupil of the eye and a second pupil of the second eye.

5. The method of claim 1 further comprising:
    adjusting a configuration of the head mounted display (HMD) for the wearer of the prescription lens based on the 3D optical-mechanical fit profile.

6. The method of claim 5, wherein fabricating the layer of the plano-concave lens for the HMD includes fabricating the plano-concave lens to couple with the element of the HMD to have the distortion profile or an adjusted distortion profile that is substantially similar to the distortion profile.

7. The method of claim 1, wherein the lens-to-eye data includes at least one of eye-relief distance, pupil size of the eye, frame tilt angle, or corneal topography of the cornea of the eye,
    wherein the eye-relief distance is from the back surface of the prescription lens to the cornea of the eye,
    and wherein the frame tilt angle measures an angle of a glasses frame that holds the prescription lens.

8. The method of claim 1, wherein capturing the volumetric depth image includes capturing a plurality of optical spectrum signals with an optical coherence tomography (OCT) system, wherein the optical spectrum signals in the plurality are generated by reflections from the front surface of the prescription lens, the back surface of the prescription lens, and the cornea of the eye.

9. The method of claim 8, wherein the OCT system is a Fourier-domain OCT system including a light source to illuminate the eye, the prescription lens, and a reference arm of the spectral-domain OCT system.

10. The method of claim 8, wherein the volumetric depth image is generated by performing a Fourier Transform of each of the optical spectrum signals to generate depth profiles that are aggregated together as the volumetric depth image.

11. The method of claim 1, wherein the volumetric depth image is generated by one of time-of-flight imaging, Light Detection and Ranging (LIDAR) imaging, or focused ultrasound imaging.

12. A system comprising:
an optical coherence tomography (OCT) device configured to capture volumetric depth images that includes a front surface of a prescription lens, a back surface of the prescription lens, and a cornea of an eye of a wearer of the prescription lens;
a memory storing instructions; and
processing logic configured to receive the volumetric depth images from the OCT device, wherein the processing logic is also configured to access the instructions that when executed by the processing logic, cause the processing logic to perform operations comprising:
determining lens-to-eye data from the volumetric depth images, wherein the lens-to-eye data includes measurements of the prescription lens with respect to the eye;
generating a three-dimensional (3D) optical-mechanical fit profile for the wearer based on the lens-to-eye data; and
generating a distortion profile based at least in part on a modulation transfer function (MTF) and/or a point spread function (PSF) of a prescription lens of the 3D optical-mechanical fit profile, wherein the distortion profile is to be used to assist in fabricating a layer of a plano-concave lens to couple with an element of a head mounted display (HMD) to substantially replicate a distortion of the wearer's existing prescription lens for reducing a period of adjustment to the HMD.

13. The system of claim 12, wherein the lens-to-eye data includes a base curve of the front surface of the prescription lens and a back curve of the back surface of the prescription lens.

14. The system of claim 12, wherein the volumetric depth images include a second prescription lens and a second eye of the wearer of the second prescription lens, and wherein the lens-to-eye data includes an interpupillary distance (IPD) between a first pupil of the eye and a second pupil of the second eye.

15. The system of claim 12, wherein the processing logic is configured to perform further operations comprising storing the distortion profile to the memory, wherein the distortion profile is linked to user data associated with the wearer of the prescription lens.

16. The system of claim 12, wherein the lens-to-eye data includes at least one of eye-relief distance, pupil size of the eye, frame tilt angle, or corneal topography of the cornea of the eye,
wherein the eye-relief distance is from the back surface of the prescription lens to the cornea of the eye,
and wherein the frame tilt angle measures an angle of a glasses frame that holds the prescription lens.

17. The system of claim 12, wherein the OCT device is a spectral-domain OCT device including a broadband light source to illuminate the eye, the prescription lens, and a reference arm of the spectral-domain OCT device.

18. A non-transitory machine-accessible storage medium that provides instructions that, when executed by processing logic, will cause the processing logic to perform operations comprising:
receiving volumetric depth images, the volumetric depth images including a front surface of a prescription lens, a back surface of the prescription lens, and a cornea of an eye of a wearer of the prescription lens;
determining lens-to-eye data from the volumetric depth images, wherein the lens-to-eye data includes measurements of the prescription lens with respect to the eye;
generating a three-dimensional (3D) optical-mechanical fit profile for the wearer based on the lens-to-eye data; and
generating a distortion profile based at least in part on a modulation transfer function (MTF) and/or a point spread function (PSF) of a prescription lens of the 3D optical-mechanical fit profile, wherein the distortion profile is to be used to assist in fabricating a layer of a plano-concave lens to couple with an element of a head mounted display (HMD) to substantially replicate a distortion of an existing prescription lens of the wearer for reducing a period of adjustment to the HMD.

19. The non-transitory machine-accessible storage medium of claim 18, the non-transitory machine-accessible storage medium providing further instruction that will cause the processing logic to perform further operations including storing the distortion profile to a memory, wherein the distortion profile is linked to user data associated with the wearer of the prescription lens.

20. The non-transitory machine-accessible storage medium of claim 18, wherein the lens-to-eye data includes a base curve of the front surface of the prescription lens and a back curve of the back surface of the prescription lens.

* * * * *